(12) United States Patent
Hsing et al.

(10) Patent No.: US 11,761,031 B2
(45) Date of Patent: Sep. 19, 2023

(54) METHOD FOR REAL TIME MONITORING OF NUCLEIC ACID AMPLICONS MEDIATED BY LOOP OLIGONUCLEOTIDE PROBES

(71) Applicant: The Hong Kong University of Science and Technology, Hong Kong (CN)

(72) Inventors: I-Ming Hsing, Hong Kong (CN); Xiao Lu, Hong Kong (CN); Henson Lim Lee Yu, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 130 days.

(21) Appl. No.: 17/333,993

(22) Filed: May 28, 2021

(65) Prior Publication Data

US 2021/0371915 A1 Dec. 2, 2021

Related U.S. Application Data

(60) Provisional application No. 63/102,048, filed on May 28, 2020.

(51) Int. Cl.
*C12Q 1/6848* (2018.01)
(52) U.S. Cl.
CPC .................. *C12Q 1/6848* (2013.01)
(58) Field of Classification Search
None
See application file for complete search history.

(56) References Cited

U.S. PATENT DOCUMENTS

| | | | |
|---|---|---|---|
| 4,629,689 A | 12/1986 | Diamond et al. | |
| 4,683,195 A | 7/1987 | Mullis et al. | |
| 5,339,491 A | 8/1994 | Sims | |
| 5,409,818 A | 4/1995 | Davey et al. | |
| 5,427,930 A | 6/1995 | Birkenmeyer et al. | |
| 2012/0058472 A1 | 3/2012 | Hsing et al. | |
| 2020/0370116 A1 | 11/2020 | Meagher et al. | |

FOREIGN PATENT DOCUMENTS

| | | |
|---|---|---|
| CN | 111719017 A | 9/2020 |
| CN | 111801426 A | 10/2020 |
| WO | WO-2020/006036 A1 | 1/2020 |

OTHER PUBLICATIONS

Tanner, Simultaneous multiple target detection in real-time loop-mediated isothermal amplification, BioTechniques, 53(2): 81-89, 2012. (Year: 2012).*
Ding, A ribonuclease-dependent cleavable beacon primer triggering DNA amplification for single nucleotide mutation detection with ultrahigh sensitivity and selectivity, Chem Commun, 55, 12623-12626, 2019. (Year: 2019).*
New England Biolabs, Isothermal Amplification—Polymerases, 2022. (Year: 2022).*
Chander, A novel thermostable polymerase for RNA and DNA loop-mediated isothermal amplification (LAMP), Frontiers in Microbiology, 5(395): 1-11, 2014. (Year: 2014).*
Gillespie, Porcine Circovirus Type 2 and Porcine Circovirus-Associated Disease, J Vet Intern Med, 23, 1151-1163, 2009. (Year: 2009).*
Notomi, T. et al., "Loop-mediated isothermal amplification of DNA", *Nucleic Acids Research*, 2000, 28(12):e63(i)-e63(vii), Oxford University Press.
Parida, M. et al., "Rapid Detection and Differentiation of Dengue Virus Serotypes by a Real-Time Reverse Transcription-Loop-Mediated Isothermal Amplification Assay", *Journal of Clinical Microbiology*, 2005, 43(6):2895-2903, American Society for Microbiology, DOI:10.1128/JCM.43.6.2895-2903.2005.
Zerilli, F. et al., "Methylation-Specific Loop-Mediated Isothermal Amplification for Detecting Hypermethylated DNA in Simplex and Multiplex Formats", *Clinical Chemistry*, 2010, 56(8):1287-1296, American Association for Clinical Chemistry.
Tanner, N.A. et al., "Simultaneous multiple target detection in real-time loop-mediated isothermal amplification", *BioTechniques*, Aug. 2012, 53(2):81-89, doi:10.2144/0000113902.
Liu, W. et al., "Establishment of an accurate and fast detection method using molecular beacons in loop-mediated isothermal amplification assay", *Scientific Reports*, 2017, 7(40125):1-9, DOI:10.1038/srep40125.
Mackay, I.M. et al., "Real-time PCR in virology", *Nucleic Acids Research*, 2002, 30(6):1292-1305, Oxford University Press.
Peto, J. et al., "Unnecessary obstacles to COVID-19 mass testing", *Lancet*, 2020, 1 page, https://doi.org/10.1016/S0140-6736(20)32170-X.
Mitchell, S.L. et al., "Understanding, verifying and implementing Emergency Use Authorization molecular diagnostics for the detection of SARS-CoV-2 RNA", *Journal of Clinical Microbiology*, 2020, 20 pages, doi:10.1128/JCM.00796-20, American Society for Microbiology.
Nordling, L., "The pandemic appears to have spared Africa so far. Scientists are struggling to explain why", Science, 2020, 5 pages, doi:10.1126/science.abe2825.
Wong, Y.P. et al., "Loop Mediated Isothermal Amplification (LAMP): A Versatile Technique for Detection of Microorganisms", *J. Appl. Microbiol.*, 2018, 124(3):626-643, doi:10.1111/jam.13647.

(Continued)

*Primary Examiner* — Angela M. Bertagna
*Assistant Examiner* — Carolyn L Greene
(74) *Attorney, Agent, or Firm* — Saliwanchik, Lloyd & Eisenschenk

(57) ABSTRACT

The subject invention pertains to the rapid amplification and real-time monitoring of nucleic acid sequences at a constant temperature. Specifically, fluorescent or electroactive-labeled loop probes and primers are designed to be specific to identified regions of a target nucleic acid sequences and subsequently amplify and permit the identification of the presence of the target sequence. In this method, a DNA polymerase with no 5' to 3' exonuclease activity is added to extend the primers and probes, while a nicking endonuclease is added to specifically identify the amplified nucleic acid product and cleave the label from the loop probe-extended DNA duplex.

18 Claims, 9 Drawing Sheets

Specification includes a Sequence Listing.

(56) References Cited

OTHER PUBLICATIONS

Hu, C. et al., "Ultra-fast electronic detection of antimicrobial resistance genes using isothermal amplification and Thin Film Transistor sensors", *Biosensors and Bioelectronics*, 2017, 96:281-287, http://dx/doi.org/10.1016/j.bios.2017.05.016.

Piepenburg, O. et al., "DNA Detection Using Recombination Proteins", *PLoS Biology*, Jul. 2006, 4(7)(e204):1115-1121.

Mori, Y. et al., "Loop-mediated isothermal amplification (LAMP): a rapid, accurate, and cost-effective diagnostic method for infectious diseases", *J. Infect. Chemother.*, 2009, 15:62-69, Japan Society of Chemotherapy and The Japanese Association for Infectious Diseases, DOI:10.1007/s10156-009-0669-9.

Tomita, N. et al., "Loop-mediated isothermal amplification (LAMP) of gene sequences and simple visual detection of products", *Nature Protocols*, 2008, 3(5):877-882, Nature Publishing Group, doi:10.1038/nprot.2008.57.

Mori, Y. et al., "Detection of Loop-Mediated Isothermal Amplification Reaction by Turbidity Derived from Magnesium Pyrophosphate Formation", Biochemical and Biophysical Research Communications, 2001, Academic Press, 289:150-154, doi:10.1006/bbrc.2001.5921.

Francois, P. et al., "Robustness of a loop-mediated isothermal amplification reaction for diagnostic applications", *FEMS Immunol. Med. Microbiol.*, 2011, 62:41-48, Federation of European Microbiological Societies Published by Blackwell Publishing Ltd., DOI:10.1111/m.1574-695X.2011.00785.x.

Dao Thi, V.L. et al., "A colorimetric RT-LAMP assay and LAMP-sequencing for detecting SARS-CoV-2 RNA in clinical samples", *Science Translational Medicine*, 2020, 12(556)(eabc7075):1-20, American Association for the Advancement of Science, doi: 10.1126/scitranslmed.abc7075.

Dao Thi, V.L. et al., "Screening for SARS-CoV-2 infections with colorimetric RT-LAMP and LAMP sequencing", *medRxiv*, 2020, 28 pages, https://doi.org/10.1101/2020.05.05.20092288.

Holland, P.M. et al., "Detection of specific polymerase chain reaction product by utilizing the 5'→3' exonuclease activity of *Thermus aquaticus* DNA polymerase", *Proc. Natl. Acad. Sci. USA*, Aug. 1991, Biochemistry, 88:7276-7280.

Zhang, Z. et al., "Direct DNA Amplification from Crude Clinical Samples Using a PCR Enhancer Cocktail and Novel Mutants of Taq", *Journal of Molecular Diagnostics*, Mar. 2010, 12(2):152-161, American Society for Investigative Pathology and the Association for Molecular Pathology, DOI:10.2353/jmoldx.2010.090070.

Klein, S.A. et al., "Comparison of TaqMan™ real-time PCR and p24 Elisa for quantification of in vitro HIV-1 replication", *Journal of Virological Methods*, 2003, 107:169-175, Elsevier Science B.V.

Yang, S. et al., "PCR-based diagnostics for infectious diseases: uses, limitations, and future applications in acute-care settings", *Lancet Infectious Diseases*, Jun. 2004, 4:337-348.

Walker, G.T. et al., "Isothermal in vitro amplification of DNA by a restriction enzyme/DNA polymerase system", *Proc. Natl. Acad. Sci. USA*, Jan. 1992, 89:392-396, Applied Biological Sciences.

Wang, H. et al., "Preparation of DNA Substrates for In Vitro Mismatch Repair", *Molecular Biotechnology*, 2000, 15:97-104, Human Press Inc.

Ganguli, A. et al., "Rapid isothermal amplification and portable detection system for SARS-CoV-2", *Proc. Natl. Acad. Sci. USA*, 2020, 117(37):22727-22735, www.pnas.org/cgi/doi/10.1073/pnas.2014739117.

Tanner, N.A. et al., "Visual detection of isothermal nucleic acid amplification using pH-sensitive dyes", *BioTechniques*, Feb. 2015, 58(2):59-68, doi:10.2144/000114253.

Goto, M. et al., "Colorimetric detection of loop-mediated isothermal amplification reaction by using hydroxyl naphthol blue", BioTechniques, Mar. 2009, 46(3):167-172, doi:10.2144/000113072.

Gadkar, V.J. et al., "Real-time Detection and Monitoring of Loop Mediated Amplification (LAMP) Reaction Using Self-quenching and De-quenching Fluorogenic Probes", *Scientific Reports*, 2018, 8(5548):1-10, DOI: 10.1038/s41598-018-23930-1.

Hardinge, P. et al., "Reduced False Positives and Improved Reporting of Loop-Mediated Isothermal Amplification using Quenched Fluorescent Primers", *Scientific Reports*, 2019, 9(7400):1-13, https://doi.org/10.1038/541598-019-43817-z.

Ding, X. et al., "Cleavable hairpin beacon-enhanced fluorescence detection of nucleic acid isothermal amplification and smartphone-based readout", *Scientific Reports*, 2020, vol. 10(18819), 9 pages, https://doi.org/10.1038/s41598-020-75795-y.

Lu, R. et al., "A Novel Reverse Transcription Loop-Mediated Isothermal Amplification Method for Rapid Detection of SARS-CoV-2", *International Journal of Molecular Sciences*, 2020, 21(2826):1-10, doi:10.3390/ijms21082826.

Patchsung, M. et al., "Clinical validation of a Cas13-based assay for the detection of SARS-CoV-2 RNA", *Nature Biomedical Engineering*, Dec. 2020, 4:1140-1149, https://doi.org/10.1038/S41551-020-00603-x.

Broughton, J.P. et al., "Rapid Detection of 2019 Novel Coronavirus SARS-CoV-2 Using a CRISPR-based DETECTR Lateral Flow Assay", *medRxiv*, 2020, 28 pages, https://doi.org/10.1101/2020.03.06.20032334.

Curtis, K.A. et al., "Sequence-Specific Detection Method for Reverse Transcription, Loop-Mediated Isothermal Amplification of HIV-1", *Journal of Medical Virology*, 2009, 81:966-972, Wiley-Liss, Inc.

Kouguchi, Y. et al., "Homogeneous, real-time duplex loop-mediated isothermal amplification using a single fluorophore-labeled primer and an intercalator dye: its application to the simultaneous detection of Shiga toxin genes 1 and 2 in Shiga toxigenic *Escherichia coli* isolates", Molecular and Cellular Probes, 2010, 24:190-195, Elsevier Ltd.

\* cited by examiner

METHOD FOR REAL TIME MONITORING OF NUCLEIC ACID AMPLICONS MEDIATED BY LOOP OLIGONUCLEOTIDE PROBES

CROSS-REFERENCE TO RELATED APPLICATION

This application claims the benefit of U.S. Provisional Application Ser. No. 63/102,048, filed May 28, 2020, which is hereby incorporated by reference in its entirety including any tables, figures, or drawings.

SEQUENCE LISTING

The Sequence Listing for this application is labeled "SeqList_05-04-2021_ST25.txt" which was created on May 4, 2021 and is 1,575 bytes. The entire content of the sequence listing is incorporated herein by reference in its entirety.

FIELD OF THE INVENTION

The present invention generally relates to the field of biochemistry and molecular biology, particularly to the real-time detection of nucleic acid targets. More particularly, the invention relates to nucleic acid probes with specific loop structures and sequence and their methods of use in nucleic acid reactions for the detection of specific nucleic acid sequence using fluorescence-based, electrochemistry-based or lateral flow-based detection techniques.

BACKGROUND OF THE INVENTION

Target nucleic acid amplification is usually a mandatory step in nucleic acid test, because the number of target nucleic acid extracted is usually too low to be accurately detected directly by existing equipment. Aside from conventional polymerase chain reaction (PCR) which requires two- or three-temperature controls, isothermal amplification methods (such as loop-mediated isothermal amplification (LAMP), helicase-dependent amplification (HDA), nucleic acid sequence-based amplification (NASBA), strand-displacement amplification (SDA), recombinase polymerase amplification (RPA); See, e.g., U.S. Pat. Nos. 4,683,195; 4,629,689; 5,427,930; 5,339,491; and 5,409,818.), which only need one reaction temperature, have been widely used in diagnostic research.

LAMP is a method for the amplification of nucleic acids, which amplifies DNA/RNA under isothermal conditions (60-65° C.) with high specificity and sensitivity using a set of six specially designed primers and a Bst DNA polymerase [1]. Many applications have employed LAMP as an amplification process, thereby proving its high yield and robustness. Compared with PCR as gold standard, it has similar sensitivity and is less susceptible to inhibitors. In some cases, the sample preparation steps required for PCR can even be eliminated[2] [3] [4]. Even if the primer design of these isothermal methods is more complex than PCR, the amplification is carried out under constant temperature conditions, and the reagents and workflow are relatively simple. At present, there have been some visual detection methods, such as detection of turbidity, colorimetric, and fluorescence signal. Typically, the measurement of LAMP products relies on end-point analysis and requires post-amplification processing, leading to possible cross-contamination or detection of non-specific LAMP amplicons. Some of these methods include: resolving amplified products on agarose gel electrophoresis[1], turbidity analysis of positive reactions due to the accumulation of magnesium pyrophosphate ($Mg_2P_2O_7$) [5], detection of dsDNA under UV-light in the presence of intercalating dyes, such as SYBR Green I or EvaGreen [6], and addition of metal ion indicators like calcein/$Mn^{2+}$ or hydroxynapthol blue dye (HNB) [7]. Among them, intercalated fluorescent dyes are favored for clinical diagnosis because of their higher sensitivity and relative tolerance to opaque substances such as proteins, which are known to affect turbidity signals. A major disadvantage, however, of using non-specific detection methods is the increased likelihood of detecting false positives. [8] Although LAMP relies on 4-6 different primers to independently identify 6-8 independent regions on the target sequence, this is at least theoretically more specific than a double primer PCR. Though the mechanism of non-specific amplification remains unclear, it is assumed that cis and trans priming amongst the six primers, could be responsible for this phenomenon. Thus, indirect detection of amplification products remains one of the major shortcomings of LAMP technology.

Fluorophore-labelled nucleic acids that specifically hybridize in a sequence dependent manner to a transiently generated single-stranded DNA structure have proven to be an ideal solution to any non-specific dye-based detection system. Examples of such include the hydrolysis-based TaqMan™ probes specifically developed for qPCR and molecular beacons. Due to the atypical amplification chemistry of LAMP seamless application of any of these probe technologies specifically developed for qPCR have proven to be technically challenging. Attempts, however, have been made to develop a probe-based detection system for LAMP, including: loss-of-signal guanine quenching [9], gain-of-signal fluorescence using labeled primers[10], detection of amplification by release of quenching (DARQ)[11], assimilating probe, and molecular beacons[12]. All these methods add one or more fluorescently-labeled probes to the LAMP reaction which are unavoidable in high background due to the limitation of their own principles. Due to the lack of 5' to 3' endonuclease activity of the Bst polymerase used in a LAMP reaction, a traditional hydrolysis fluorescence-quencher probe cannot be used to solve the problem of high background, which affects the specificity of a LAMP reaction.

Therefore, there remains a need for a probe that can be used for real-time nucleic acid detection with reduced background detection.

BRIEF SUMMARY OF THE INVENTION

The subject invention pertains to a loop-labeled probe with specific sequence design and structure is presented to general directed to the rapid amplification and real time monitoring of nucleic acid sequences at a constant temperature. Specifically, a hydrolysis probe can be used in electrochemical nucleic acid detection. In addition, it depends on the principle of immobilization-free biosensor, and qualitative analysis based on the principle of diffusion coefficient difference of nucleic acid fragments before and after hydrolysis. There is no quenching group like fluorescent probe which can reduce the noise, so it affects the sensitivity. This method has the compatibility of lateral flow target specific nucleic acid detection, especially, with numerous advantageous and novel subject composition methods that employ a constant temperature and visual readout. Thus, we propose a new method with Loop-labeled probe to enhance sensitivity and specificity in isothermal amplification and detection.

BRIEF DESCRIPTION OF THE SEQUENCES

Figure 1A:
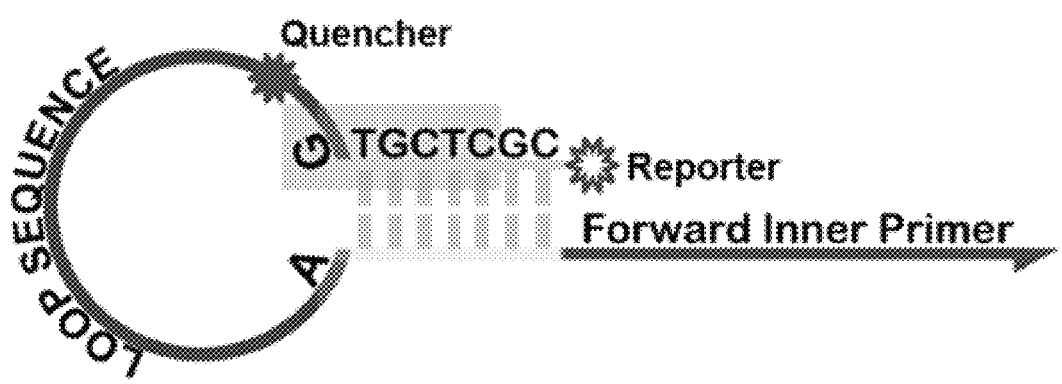
FIG. 1A. Detection principle scheme. The structure of the fluorescent loop probe contains a fluorophore at the 5' end (reporter) and the corresponding quencher located in the loop structure to ensure that the probe is in the quenched state. The stem region contains the nicking enzyme recognition sequence. The mismatch is introduced into the last G base so that it is not cleaved in the absence of the target nucleic acid. 5' CG dimer was added to the end of the stem to increase the stability of the double stranded region.

SEQ ID NO: 1: Forward primer (FP) to detect *Salmonella* spp. Sul1 gene using a fluorescent electrochemical, or lateral flow readout.

SEQ ID NO: 2: Backward primer (BP) to detect *Salmonella* spp. Sul1 gene using a fluorescent electrochemical, or lateral flow readout.

SEQ ID NO: 3: Loop probe (LP) to detect *Salmonella* spp. Sul1 gene using a fluorescent readout defined by the labels attached to the nucleotide sequence.

SEQ ID NO: 4: Loop probe (LP) to detect *Salmonella* spp. Sul1 gene using fluorescent, electrochemical, or lateral flow readout defined by the labels attached to the nucleotide sequence. From 5' to 3', the LP contains a reporter, nicking enzyme recognition site, loop sequence, and one mismatch with nicking enzyme recognized site at 5 prime, and forward inner primer which is entirely complementary with target sequence, SEQ ID NO: 5: Assistant probe (AP) shown as a harpin with backward inner primer at the 3 prime end, which is completely homologous with target sequence to detect *Salmonella* spp. Sul1 gene using fluorescent, electrochemical or lateral flow readout.

DETAILED DISCLOSURE OF THE INVENTION

Selected Definitions

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of," "consisting," and "consists."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed.

In the present disclosure, ranges are stated in shorthand, to avoid having to set out at length and describe each and every value within the range. Any appropriate value within the range can be selected, where appropriate, as the upper value, lower value, or the terminus of the range. For example, a range of 1-10 represents the terminal values of 1 and 10, as well as the intermediate values of 2, 3, 4, 5, 6, 7, 8, 9, and all intermediate ranges encompassed within 1-10, such as 2-5, 2-8, and 7-10. Also, when ranges are used herein, combinations and sub-combinations of ranges (e.g., subranges within the disclosed range) and specific embodiments therein are intended to be explicitly included.

As used herein and in the claims, a "sample" refers to a sample of cell, tissue or fluid, including but not limited to, for example, skin, plasma, serum, spinal fluid, lymph fluid, synovial fluid, urine, tears, blood cells, organs, tumors, environmental sources, including waterways, soil, or air, samples of in vitro cell culture constituents (including but not limited to conditioned medium resulting from the growth of cells in cell culture medium, recombinant cells and cell components), or any other source derived from an organism or containing an organism.

The term "organism" as used herein includes viruses, bacteria, fungi, plants and animals. Additional examples of organisms are known to a person of ordinary skill in the art and such embodiments are within the purview of the materials and methods disclosed herein. The assays described herein can be useful in analyzing any genetic material obtained from any organism.

The term "genome", "genomic", "genetic material" or other grammatical variation thereof as used herein refers to genetic material from any organism. A genetic material can be viral genomic DNA or RNA, nuclear genetic material, such as genomic DNA, or genetic material present in cell organelles, such as mitochondrial DNA or chloroplast DNA. It can also represent the genetic material coming from a natural or artificial mixture or a mixture of genetic material from several organisms.

A "target sequence" as used herein is a polynucleotide (e.g., as defined herein, including a DNA, RNA, or DNA/RNA hybrid, as well as modified forms thereof) that includes a "target site." The terms "target site" is used to refer to a nucleic acid sequence present in a target genomic sequence (e.g., DNA or RNA in a host or pathogen) to which a primer (e.g., any herein) will bind provided sufficient conditions (e.g., sufficient complementarity) for binding exist.

Suitable DNA/RNA binding conditions include physiological conditions normally present in a cell. Other suitable DNA/RNA binding conditions (e.g., conditions in a cell-free system) are known in the art.

The term "hybridizes with" when used with respect to two sequences indicates that the two sequences are sufficiently complementary to each other to allow nucleotide base pairing between the two sequences. Sequences that hybridize with teach other can be perfectly complementary but can also have mismatches to a certain extent. Therefore, the sequences at the 5' and 3' ends of the loop and assistant probes and forward and backward primers described herein may have a few mismatches with the corresponding target sequences at the 5' and 3' ends of the target nucleotide region as long as the loop and assistant probes and forward and backward primers can hybridize with the target sequences. Depending upon the stringency of hybridization, a mismatch of up to about 5% to 20% between the two complementary sequences would allow for hybridization between the two sequences. Typically, high stringency conditions have higher temperature and lower salt concentration, and low stringency conditions have lower temperature and higher salt concentration. High stringency conditions for hybridization are preferred.

"Hybridizing conditions" refer to conditions of temperature, pH, and concentrations of reactants that allow at least a portion of complementary sequences to anneal with each other. Conditions required to accomplish hybridization depend on the size of the oligonucleotides to be hybridized, the degree of complementarity between the oligonucleotides and the presence of other materials in the hybridization reaction admixture. The actual conditions necessary for each hybridization step are well known in the art or can be readily determined by a person of ordinary skill in the art. Typical hybridizing conditions include the use of solutions buffered to a pH from about 7 to about 8.5 and temperatures of from about 30° C. to about 80° C. Hybridization conditions may also include a buffer that is compatible, i.e., chemically inert, with respect to the oligonucleotides and other components, yet still allows for hybridization between complementary base pairs.

A "primer" is an oligonucleotide capable of initiating synthesis of nucleic acid sequence in a nucleic acid amplification reaction. A primer initiates nucleic acid amplification when placed under conditions in which synthesis is induced of a primer extension product that is complementary to a template nucleic acid strand. Such conditions include provision of appropriate nucleotides, an enzyme for polymerization such as a DNA polymerase, an appropriate buffer and a suitable temperature. Primers are synthesized based on the sequence of a target locus. For example, based on the sequence of a target locus and the sequences flanking the target locus, a skilled artisan can determine the sequence of a primer or a primer pair for amplification of the target locus.

A primer pair is a pair of oligonucleotides and designed to amplify a specific locus from a template nucleotide sequence material. Guidelines for designing a primer pair to amplify a specific locus to in a template genetic material are well known in the art.

As used herein, the phrases "operably linked" or "operatively linked" or "operatively associated with," as used interchangeably, refers to a juxtaposition wherein the components so described are in a relationship permitting them to function in their intended manner. A first component can be operably linked to a second component by way of any useful bond (e.g., a covalent bond, a non-covalent bond, and/or linked via van der Waals forces, hydrogen bonds, and/or other intermolecular forces, such as those including a π-π interaction, a salt bridge, or a cation-π interaction) or any useful linker (e.g., any herein).

Throughout this disclosure, different sequences are described by specific nomenclature, for example, a primer binding sequence, primer sequence, target sequence, and probe sequence. When such nomenclature is used, it is understood that the identified sequence is substantially identical or substantially reverse complementary to at least a part of the corresponding sequence. For example, "a primer sequence" describes a sequence that is substantially identical to at least a part of the primer sequence or substantially reverse complementary to at least a part of the primer sequence. This is because when a captured target genomic region is converted into a double stranded form comprising the primer binding sequence, the double stranded target genomic region can be sequenced using a primer having a sequence that substantially identical or substantially reverse complementary to at least a part of primer binding sequence. Thus, the nomenclature is used herein to simplify the description of different polynucleotides and parts of polynucleotides used in the methods disclosed here; however, a person of ordinary skill in the art would recognize that appropriate substantially identical or substantially reverse complementary sequences to at least a part of the corresponding sequences could be used to practice the methods disclosed herein.

Also, two sequences that correspond to each other, for example, a primer binding sequence and a primer sequence or a sequencing primer binding sequence and a sequencing primer sequence, have at least 90% sequence identity, preferably, at least 95% sequence identity, even more preferably, at least 97% sequence identify, and most preferably, at least 99% sequence identity, over at least 70%, preferably, at least 80%, even more preferably, at least 90%, and most preferably, at least 95% of the sequences. Alternatively, two sequences that correspond to each other are reverse complementary to each other and have at least 90% perfect matches, preferably, at least 95% perfect matches, even more preferably, at least 97% perfect matches, and most preferably, at least 99% perfect matches in the reverse complementary sequences, over at least 70%, preferably, at least 80%, even more preferably, at least 90%, and most preferably, at least 95% of the sequences. Thus, two sequences that correspond to each other can hybridize with each other or hybridize with a common reference sequence over at least 70%, preferably, at least 80%, even more preferably, at least 90%, and most preferably, at least 95% of the sequences. Preferably, two sequences that correspond to each other are 100% identical over the entire length of the two sequences or 100% reverse complementary over the entire length of the two sequences.

The disclosure provides material and methods that solve the problems associated with conventional methods for real-time analysis monitoring of amplifying nucleic acids sequences, while minimizing interfering background.

Target Sequence Amplification

The methods disclosed herein provide amplifying a target nucleotide sequence. The methods comprise providing a target DNA nucleotide sequence, an outer pair of primers comprising a forward primer (FP) and a backward primer (BP), and an inner pair of primers comprising a loop probe (LP) and an assistant probe (AP), wherein, the FP and the LP can bind to the same strand of the target nucleotide sequence, which is preferably a double-stranded DNA (dsDNA) template, while the BP and AP bind on the opposite strand. Optionally, the inner primers, LP and AP, are rationally designed such that they are thermodynamically favored to bind to its complementary region first compared to its outer primer counterpart, FP and BP respectively.

In certain embodiments, the loop probe comprises a first nucleic acid sequence having sufficient complementarity to a first site in the target nucleic acid operably linked to a label and operably linked to two or more endonuclease binding sites, wherein one of the two or more endonuclease binding sites have at least one substituted base pair that inhibits endonuclease digestion of the loop probe, and the assistant probe comprises a second nucleic acid sequence having sufficient complementarity to a second site of the target nucleic acid; and the forward primer and the backward primer are complementary to at least a portion of said target nucleic acid. In preferred embodiments, the assistant probe and backwards primer are complementary to a sequence downstream from the loop probe, while the forward primer is complementary to a sequence upstream from the loop probe.

The initial reaction mixture can, in addition to template DNA and probes and primers, further comprise, one or more reagents, such as LAMP reagents (for a target DNA) or RT-LAMP reagents (for a target RNA), one or more enzymes (polymerase, reverse transcriptase, endonuclease, including a nicking endonuclease), buffer, water salt, nucleotides, divalent cations (e.g., $Mg^{++}$), or enhancing agents (e.g., betaine, dimethyl sulfoxide, ethylene glycol, glycerol, formamide, 7-deaza-2'-deoxyguanosine 5'-triphosphate, 2'-deoxyinosine 5'-triphosphate, or 1,2-propanediol). The mixture can be incubated for any useful time, such as about at least 10 minutes, 20 minutes, 30 minutes, 40 minutes, 50 minutes, 60 minutes, 70 minutes, 80 minutes, 90 minutes, or longer. In certain embodiments, the incubation time is about 10 minutes to about 120 minutes, about 20 minutes to about 90 minutes, about 30 minutes, to about 75 minutes. In certain embodiments, the reaction mixture is at any useful temperature such as, for example, from about 55° C. to about 75° C., about 60° C. to about 65° C., or, preferably, about 61° C. to about 63° C. to promote amplification. The reactions can be performed using a real-time PCR.

Figure 2A:
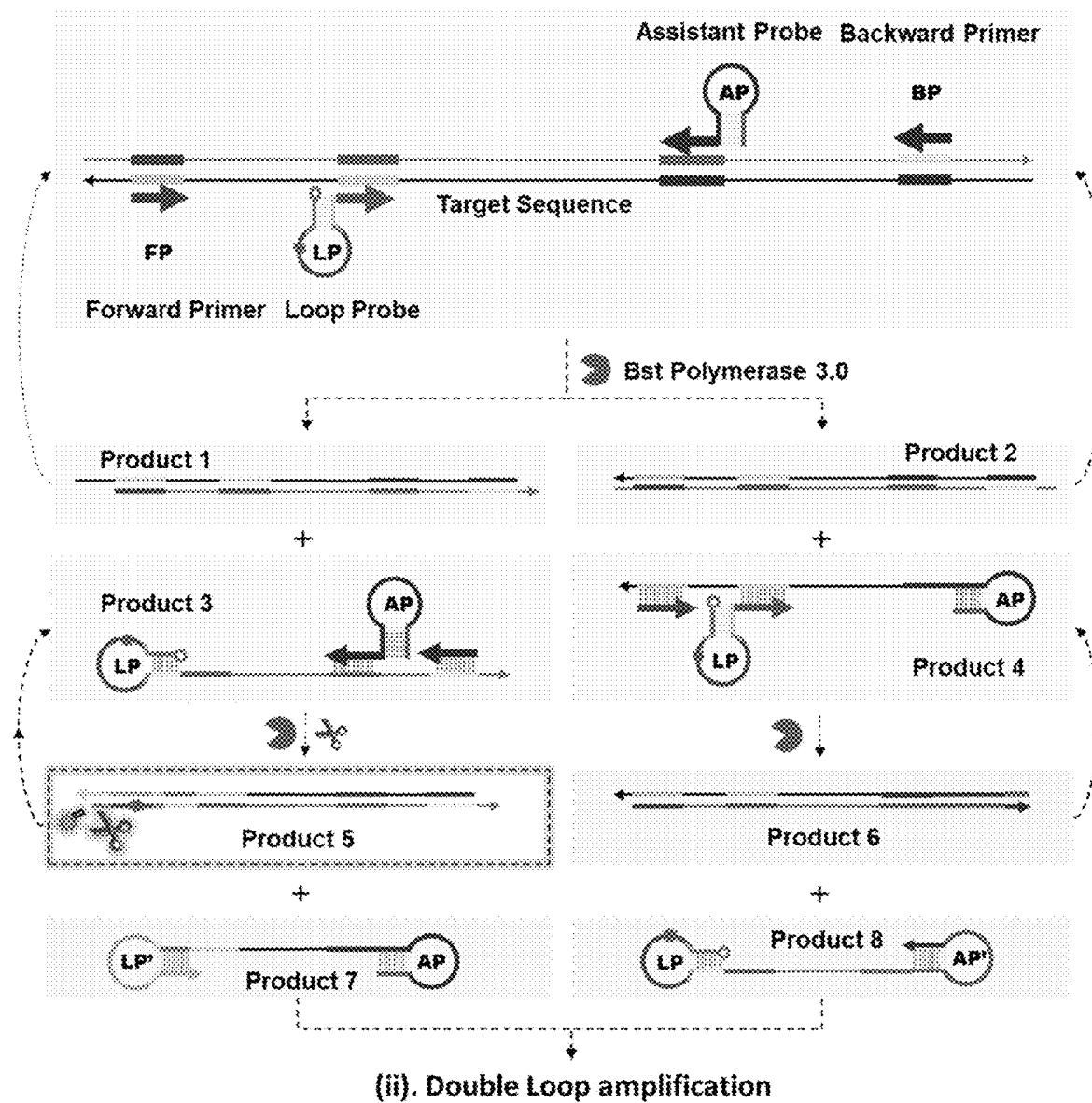
FIG. 2A. Detection scheme using a fluorescent loop probe. Pre-amplification process. The DNA template is selected to have two pairs of primer binding sites—an outer pair of forward and backward primers (FP and BP), and an inner pair of primers consisting of a loop probe (LP) and an assistant probe (AP). The inner primers, LP and AP, are rationally designed such that they are thermodynamically favored to bind to its complementary region first compared to its outer primer counterpart FP and BP, respectively.

In certain embodiments, the detection process can begin with a pre-amplification step wherein the constant hybridization and rehybridization of the dsDNA template at around, for example, about 60° C. to about 65° C., allows one of the inner primers (e.g., LP or AP) to bind and anneal to its complimentary region on the target DNA, and initiate DNA synthesis using a polymerase. When the loop probe (LP) binds to the target DNA, the synthesized complementary strand is shorter than the template, thus exposing a forward primer (FP)-binding site on the template strand but upstream of the LP-binding site. When the FP is extended by a DNA polymerase without exonuclease activity, product 1 is synthesized (FIG. 2A), the previously bound LP-containing segment (product 3; FIG. 2A) is displaced from the template strand, and the final structure of product 1 (FIG. 2A) is a double-stranded DNA (dsDNA) formed by the template and FP-primed synthesized sequence, and can participate in another cycle of LP-primer binding and extension.

Figure 2B:
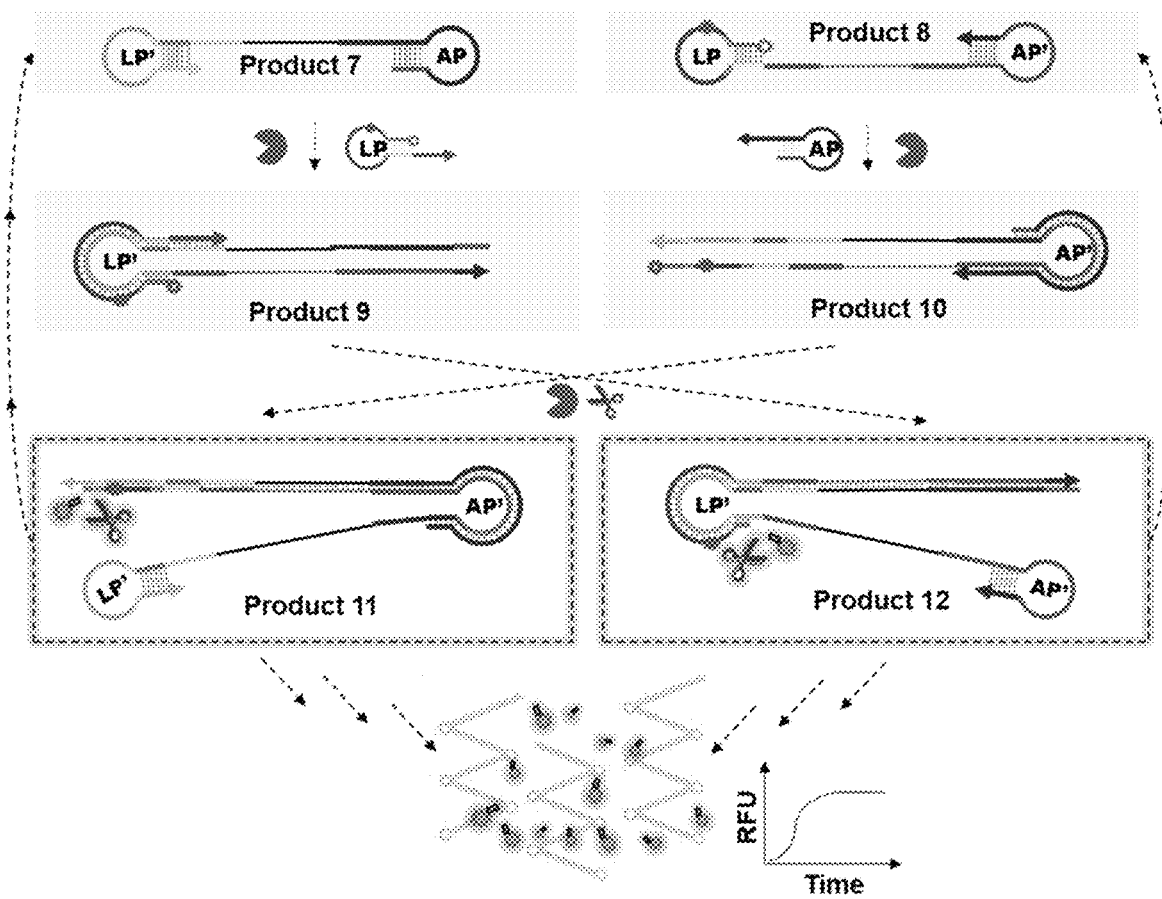
FIG. 2B. Detection scheme using a fluorescent loop probe, showing the process and signal readout principle of double loop amplification.

The single-stranded LP-containing strand (product 3; FIG. 2A), which was displaced in the previous step and has a sequence complementary to the template in the previously described cycle, can serve as a template for the reverse inner primer, AP, which forms a shorter complementary strand similar to the aforementioned LP-primed sequence (product 3; FIG. 2A), and exposes the backward primer (BP)-binding site on the same strand but upstream to the AP-binding site. The extension of the BP forms a double-stranded DNA (product 5; FIG. 2A), which now contains the double-stranded nicking site, and therefore can release a signal based on the cleaved label by an endonuclease digestion, preferably using a nicking endonuclease. The cleaved label can include an electroactive or a fluorescent label. Meanwhile, the AP-containing strand which was displaced due to the extension of the BP primer, forms a single-stranded DNA flanked by an AP-containing sequence at the 5' end, and a complement to the LP sequence (LP') at the 3' end. The AP and LP' segments will then spontaneously adopt a double looped structure (product 7; FIG. 2B) at both termini.

The entire process can happen when the AP probe binds first instead of the LP, as described above, except that the final double-loop product (product 8; FIG. 2B) will contain LP and AP' (complement sequence of AP) loops instead. In either case, the double looped structure can then proceed to the amplification phase in the next step.

In certain embodiments, both the product 7 (FIG. 2B) and the product 8 (FIG. 2B) with double-loop products derived from the pre-amplification process can be then be extended from the 3' end of the double looped structure, e.g. LP', forming a hairpin structure with an extended stem region and the other loop (product 9 and product 10, respectively; FIG. 2B), such as, for example, the AP loop, will be linearized. Then, an excess of the LP probes present in the reaction mixture can also bind to the LP' loop present and can also get extended by the polymerase, forming a double-stranded product with a displaced single-stranded region from the extension of the previous step. The single stranded region has an AP structure which then turn into a loop structure, and the cycle continues in a similar fashion described: the cycle continues to form product 9 (FIG. 2B), which happens in a similar process to the formation of product 10 (FIG. 2B) described above, but using the excess AP probe instead of LP probe. The final amplified structure will be a long dsDNA structure of tandem repeats of LP'-target-AP-target, with each target sequence being the same sequence. Lastly, every loop-probe region (LP' and AP) will contain a restriction enzyme digestion site that upon digestion, will release a fluorescent label or an electroactive label. The same structure can be obtained when starting from the LP-AP' containing looped probe, but with a tandem repeat of LP-target-AP'-target instead.

Primer and Probe Design and Detection

In certain embodiments, primers can be designed to hybridize to the target nucleic acid sequence, or portions thereof, as well as amplicons derived from the target nucleic acid sequence. In certain embodiments, the complementary nucleotide segment of the primer or probe is 5, 10, 11, 12, 13, 14, 15, 16, 17, 18, 19, 20, 21, 22, 23, 24, 25, 30, 40, 50, or 100 base pairs long, or longer. Furthermore, the primer (e.g., any herein, such as an inner primer, outer primer, or loop primer, assistant primer) can be labeled with a fluorescent label (e.g., for use with a quench probe), electroactive label, or can be unlabeled. The primer or probes can have an endonuclease binding site. The concentration of the primer and probes can be optimized to promote the amplification reaction.

In certain embodiments, the primers and probes herein can include any useful label, including fluorescent labels and quencher labels at any useful position in the nucleic acid sequence, such as, for example at the 3'- and/or 5'-terminus or within the loop structure of a probe. Exemplary fluorescent labels include a quantum dot, a fluorophore. Examples of fluorescence labels for use in this method includes fluorescein, 6-FAM™ (Applied Biosystems, Carlsbad, Calif.), TET™ (Applied Biosystems, Carlsbad, Calif.), VIC™ (Applied Biosystems, Carlsbad, Calif.), MAX, HEX™ (Applied Biosystems, Carlsbad, Calif.), TYE™ (ThermoFisher Scientific, Waltham, Mass.), TYE665, TYE705, TEX, JOE, Cy™ (Amersham Biosciences, Piscataway, N.J.) dyes (Cy2, Cy3, Cy3B, Cy3.5, Cy5, Cy5.5, Cy7), Texas Red® (Molecular Probes, Inc., Eugene, Oreg.), Texas Red-X, AlexaFluor® (Molecular Probes, Inc., Eugene, Oreg.) dyes (AlexaFluor 350, AlexaFluor 405, AlexaFluor 430, AlexaFluor 488, AlexaFluor 500, AlexaFluor 532, AlexaFluor 546, AlexaFluor 568, AlexaFluor 594, AlexaFluor 610, AlexaFluor 633, AlexaFluor 647, AlexaFluor 660, AlexaFluor 680, AlexaFluor 700, AlexaFluor 750), DyLight™ (ThermoFisher Scientific, Waltham, Mass.) dyes (DyLight 350, DyLight 405, DyLight 488, DyLight 549, DyLight 594, DyLight 633, DyLight 649, DyLight 755), ATTO™ (ATTO-TEC GmbH, Siegen, Germany) dyes (ATTO 390, ATTO 425, ATTO 465, ATTO 488, ATTO 495, ATTO 520, ATTO 532, ATTO 550, ATTO 565, ATTO Rho101, ATTO 590, ATTO 594, ATTO 610, ATTO 620, ATTO 633, ATTO 635, ATTO 637, ATTO 647, ATTO 647N, ATTO 655, ATTO 665, ATTO 680, ATTO 700, ATTO 725, ATTO 740), BODIPY® (Molecular Probes, Inc., Eugene, Oreg.) dyes (BODIPY FL, BODIPY R6G, BODIPY TMR, BOPDIPY 530/550, BODIPY 558/568, BODIPY 564/570, BODIPY 576/589, BODIPY 581/591, BODIPY 630/650, BODIPY 650/665), HiLyte Fluor™ (AnaSpec, Fremont, Calif.) dyes (HiLyte Fluor 488, HiLyte Fluor 555, HiLyte Fluor 594, HiLyte Fluor 647, HiLyte Fluor 680, HiLyte Fluor 750), AMCA, AMCA-S, Cascade® Blue (Molecular Probes, Inc., Eugene, Oreg.), Cascade Yellow, Coumarin, Hydroxycoumarin, Rhodamine Green™-X (Molecular Probes, Inc., Eugene, Oreg.), Rhodamine Red™-X (Molecular Probes, Inc., Eugene, Oreg.), Rhodamine 6G, TMR, TAMRA™ (Applied Biosystems, Carlsbad, Calif.), 5-TAMRA, ROX™ (Applied Biosystems, Carlsbad, Calif.), Oregon Green® (Life Technologies, Grand Island, N.Y.), Oregon Green 500, IRDye® 700 (Li-Cor Biosciences, Lincoln, Nebr.), IRDye 800, WellRED D2, WellRED D3, WellRED D4, and Lightcycler® 640 (Roche Diagnostics GmbH, Mannheim, Germany). In some embodiments, bright fluorophores with extinction coefficients >50,000 $M^{-1}$ $cm^{-1}$ and appropriate spectral matching with the fluorescence detection channels can be used.

In certain embodiments, a fluorescently labeled primer or probe is included in a reaction mixture and a fluorescently labeled reaction product is produced. Fluorophores used as labels to generate a fluorescently labeled primer included in embodiments of methods and compositions of the present invention can be any of numerous fluorophores including, but not limited to, 4-acetamido-4'-isothiocyanatostilbene-2, 2' disulfonic acid; acridine and derivatives such as acridine and acridine isothiocyanate; 4-amino-N-[3-vinylsulfonyl) phenyl]naphthalimide-3,5 disulfonate, Lucifer Yellow VS; N-(4-anilino-1-naphthyl)maleimide; anthranilamide, Brilliant Yellow; BIODIPY fluorophores (4,4-difluoro-4-bora-3a,4a-diaza-s-indacenes); coumarin and derivatives such as coumarin, 7-amino-4-methylcoumarin (AMC, Coumarin 120), 7-amino-4-trifluoromethylcoumarin (Coumaran 151); cyanosine; DAPDXYL sulfonyl chloride; 4',6-diaminidino-2-phenylindole (DAPI); 5',5''-dibromopyrogallol-sulfonephthalein (Bromopyrogallol Red); 7-diethylamino-3-(4 sothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-4'-dimethylaminophenylazo)benzoic acid (DABCYL); 4-dimethylaminophenylazophenyl-4'-isothiocyanate (DABITC); EDANS (5-[(2-aminoethyl)amino]naphthalene-1-sulfonic acid), eosin and derivatives such as eosin isothiocyanate; erythrosin and derivatives such as erythrosin B and erythrosin isothiocyanate; ethidium such as ethidium bromide; fluorescein and derivatives such as 5-carboxyfluorescein (FAM), hexachlorofluorescenin, 5-(4,6-dichlorotriazin-2-yl)aminofluorescein (DTAF), 2',7'-dimethoxy-4',5'-dichloro-6-carboxyfluorescein (JOE) and fluorescein isothiocyanate (FITC); fluorescamine; green fluorescent protein and derivatives such as EBFP, EBFP2, ECFP, and YFP; IAEDANS (5-({2-[(iodoacetyl)amino]ethyl} amino)naphthalene-1-sulfonic acid), Malachite Green isothiocyanate; 4-methylumbelliferone; orthocresolphthalein; nitrotyro sine; pararosaniline; Phenol Red; B-phycoerytnin; o-phthaldialdehyde; pyrene and derivatives such as pyrene butyrate, 1-pyrenesulfonyl chloride and succinimidyl 1-pyrene butyrate; QSY 7; QSY 9; Reactive Red 4 (Cibacron® Brilliant Red 3B-A); rhodamine and derivatives such as 6-carboxy-X-rhodamine (ROX), 6-carboxyrhodamine (Rhodamine 6G), rhodamine isothiocyanate, lissamine rhodamine B sulfonyl chloride, rhodamine B, rhodamine 123, sulforhodamine B, sulforhodamine 101 and sulfonyl chloride derivative of sulforhodamine 101 (Texas Red); N,N,N',N-tetramethylcarboxyrhodamine (TAMRA); tetramethyl rhodamine; tetramethyl rhodamine isothiocyanate (TRITC); riboflavin; rosolic acid and terbium chelate derivatives. In certain embodiments, the concentration of the fluorescent probe or primer in the compositions and method of use is about 0.01 µM to about 100 µM, about 0.1 µM to about 100 µM, about 0.1 µM to about 50 µM, about 0.1 µM to about 10 µM, or about 1 µM to about 10 µM. In certain embodiments, the concentration of the fluorescent probe or primer is about 0.01 µM, 0.1 µM, 1 µM, 1.1 µM, 1.2 µM, 1.3 µM, 1.4 µM, 1.5 µM, 1.6 µM, 1.7 µM, 1.8 µM, 1.9 µM, 2 µM, 2.5 µM, or 5 µM.

Exemplary quencher labels include a fluorophore, a quantum dot, a metal nanoparticle, etc.). Suitable quenchers include Black Hole Quencher®-1 (Biosearch Technologies, Novato, Calif.), BHQ-2, Dabcyl, Iowa Black® FQ (Integrated DNA Technologies, Coralville, Iowa), IowaBlack RQ, QXL™ (AnaSpec, Fremont, Calif.), QSY 7, QSY 9, QSY 21, QSY 35, IRDye QC, BBQ-650, Atto 540Q, Atto 575Q, Atto 575Q, MGB 3' CDPI3, and MGB-5' CDPI3. In one instance, the term "quencher" refers to a substance which reduces emission from a fluorescent donor when in proximity to the donor. In preferred embodiments, the quencher is within 1, 2, 3, 4, 5, 6, 7, 8, 9, 10, 11, 12, 13, 14, 15, 16, 17, 18, 19, 20, 25, or 30 nucleotide bases of the fluorescent label. Fluorescence is quenched when the fluorescence emitted from the fluorophore is detectably reduced, such as reduced by 10%, 20%, 30%, 40%, 50%, 60%, 70%, 80%, 90%, 95%, 99% or more. Numerous fluorophore quenchers are known in the art, including, dabcyl; sulfonyl chlorides such as dansyl chloride; and Black Hole Quenchers BHQ-1, BHQ-2 and BHQ-3.

In certain embodiments, an electroactively labeled primer or probe is included in a reaction mixture and an electroactively labeled reaction product is produced. Electroactive reporters can be used as labels to generate an electroactively labeled probe or primer included in embodiments of methods and compositions of the present invention can be any of numerous Electroactive reporters including, but not limited to methylene blue, Anthraquinone, Ru(bpy)2dppz2+, Ru(phen)2dppz2+, Ferrocene derivative, hematoxylin, magnetic bead, QD, biotin-advinHRP, nano composite and ferrocene. In certain embodiments, the concentration of the electroactive probe or primer in the compositions and method of use is about 0.01 µM to about 100 µM, about 0.1 µM to about 100 µM, about 0.1 µM to about 50 µM, about 0.1 µM to about 10 µM, or about 1 µM to about 10 µM. In certain embodiments, the concentration of the electroactive probe or primer is about 0.01 µM, 0.1 µM, 1 µM, 1.1 µM, 1.2 µM, 1.3 µM, 1.4 µM, 1.5 µM, 1.6 µM, 1.7 µM, 1.8 µM, 1.9 µM, 2 µM, 2.5 µM, or 5 µM.

Other labels can be used in the subject in invention, including those that permit colorimetric, and chemiluminescent or fluorescent detection. For example, biotin or digoxin are well-known in the art and can be used in conjunction with, anti-digoxin antibodies and streptavidin that are couple to alkaline phosphatase, horseradish peroxidase, or fluorescein or rhodamine (as described above), to permit colorimetric, and chemiluminescent or fluorescent detection.

Any detection method or system operable to detect a labeled reaction product can be used in methods according to embodiments of the present invention and such appropriate detection methods and systems are well-known in the art. In certain embodiments, the target nucleotide sequences can be detected directly or detected indirectly via a cleaved probe in which the labelled end of the probe is released as a cleavage product. Detection of the amplified nucleic acid or cleave produce may be performed by a method selected from the group consisting of gel electrophoresis, intercalating dye detection, PCR, real-time PCR, fluorescence, Fluorescence Resonance Energy Transfer (FRET), mass spectrometry, lateral flow assay, colorimetric assays, and CRISPR-based detection system. A signal from the fluorescently labeled reaction product is detected, for instance, using a photodiodes.

In preferred embodiments, the presence of a target nucleic acid is determined indirectly via a label that is cleaved from a probe. In certain embodiments, in the present of target, the loop probe is cleaved and the 5' end label is released as a cleavage product. The detection of this cleaved label can be performed in using a variety of well-known methods. Examples of detection methods include electroactive assay, fluorescent assay, or a lateral-flow assay. In a fluorescent or electroactive assay, every amplified loop-probe region can contain a nicking site that a restriction enzyme, such as, for example, Nb.BssSI, can recognize. Upon restriction enzyme cleavage, a fluorophore or electroactive reporter can be released. A signal from the electroactively labeled reaction can be detected, for instance, using a carbon screen-printed electrode or any other electrochemical label-based bioassay. Two types of using a carbon screen printed electrode can be used in the subject methods. The first type includes running the reaction on an incubator or PCR thermocycler, and, after that, dropping an appropriate volume of the reaction solution onto the electrode surface, ensuring that all the electrodes (working electrode, counter electrode and reference electrodes) are well covered by the reaction solution. Then, the electrochemical signal of the no template control (NTC) and the sample using electrochemical station can be recorded. The second type includes conducting the reaction into an electrochemical detection chamber with the carbon screen parented electrode under the cell. Then, the electrochemical signal changes using electrochemical station in real-time can be recorded. In preferred embodiments, the isothermal amplification reaction mixture comprising the primers, probes, and the target is first incubated at the optimum temperature of about 60° C. to about 65° C. to promote the amplification of the target, followed by taking an aliquot of the said reaction and dropping it onto an electrode surface such as carbon screen-printed electrode. Electochemical signals obtained by differential pulse voltammetry (DPV) can then be obtained using an electrochemical station. The DPV measurements can be carried out using a pulse amplitude of 100 mV/s and a scan rate of 25 mV/s. In certain embodiments, a gold electrode or disk electrode may be suitable as electrode surface, and amperometric or other voltammetric methods. DPV measurements may also be carried out at a range of pulse amplitudes from 50 to 200 mV/s and scan rates from 5 to 50 mV/s. Example of the use of electroactively labelled probes and primers and methods of detections of said probes and primers are described in the art, for example, in U.S. Pat. No. 8,975,025, which is in incorporated by reference in its entirety.

Figure 5A:
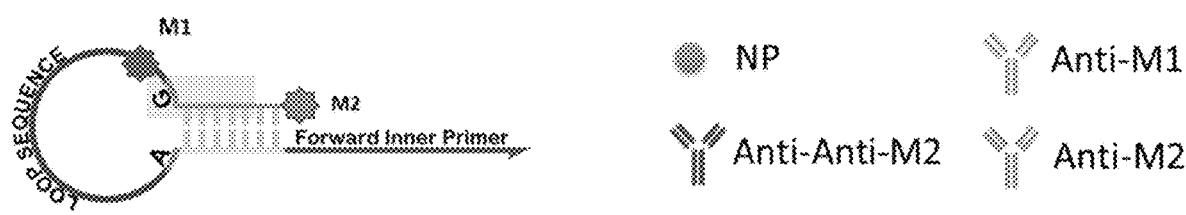
FIG. 5A Detection scheme using lateral flow assay. The loop probe with 5' end modification and inner modification. The modification could be molecules like 6-FAM, biotin or digoxin that have specific binding antibody or molecule like streptavidin for biotin.
Figure 5B:
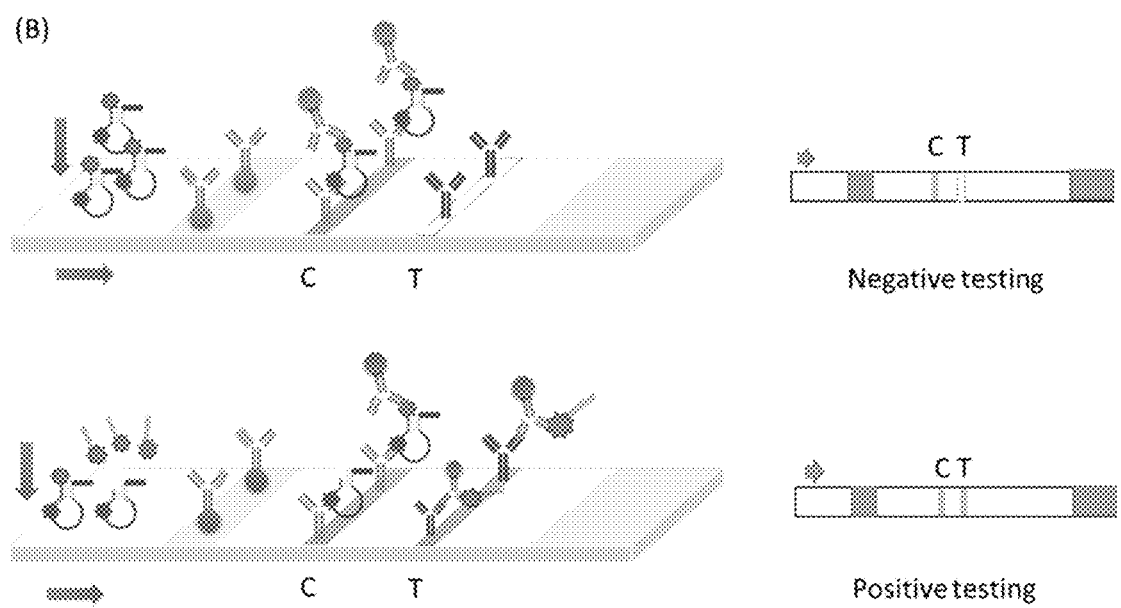
FIG. 5B Detection scheme using lateral flow assay. Scheme of signal-on design. M1, inner modification. In the absence of target, the loop probe is not cleaved, and it would bind to the antibody-conjugated nanoparticles and be immobilized onto the control band. In the present of target, the loop probe is cleaved and the 5' end label is released as cleavage product. It would bind to the nanoparticles, flow through the control band, and get strapped by the test band. Therefore, the test band would appear in the presence of target. (M2, 5' end modification. Anti-M1, antibody or molecule that specifically binds to M1. Anti-M2, antibody or molecule that specifically binds to M2. Anti-Anti-M1, antibody or molecule that specifically binds to Anti-M1. NP, antibody conjugated nanoparticles that shows color or fluorescence, such as gold nanoparticle, colored polystyrene latex particles, quantum dot, etc. T, test band. C, control band.)

In a lateral flow assay, for example, the sample could be passed across a surface that has a recognition element, including nucleic acids, or, preferably, antibodies. The lateral-flow assay can be either a sandwich or competitive assay. In certain embodiments, the cleaved label that results from the presence of a target nucleotide would bind with antibody-conjugated nanoparticles, flow through the control band, and get stopped by the test band. Therefore, the test band would appear in the presence of target. In the absence of target, the loop probe is not cleaved, and it would bind to the antibody-conjugated nanoparticles and be trapped by the control band. FIG. 5B provides a non-limiting example of a detection scheme using a lateral flow assay.

In certain embodiments, a probe or primer in the reaction can have at least one, two, three, four, or more sequences that facilitate further processing or detection. Such sequences include restriction enzyme or endonuclease sites, particularly, nicking endonuclease sites. Exemplary nicking endonuclease enzymes include Nb BsrDI, Nt.BspQI, Nt.CviPII, Nt.BstNBI, Nb.Btsl, Nt.AlwI, Nb.BbvCI, Nt.BbvCI, Nb.Bsml, Nb.BssSI, and Nt.BsmAI. In preferred embodiments, at least one of the endonuclease sites has a nucleotide substitution, addition, or deletion of at least one, two, three, four, five, six, ore more nucleotide when compared to a nucleotide sequence that can be recognized by an endonuclease. The nucleotide modification can inhibit endonuclease recognition of the site. In preferred embodiments, the probe or primer has two endonuclease binding sites and one of the binding sites, preferably a site operably linked to a label, has a site that can be recognized by an endonuclease when a complementary strand of DNA is hybridized to the probe of primer, while the other endonuclease binding site, preferably a site downstream from the site operably linked to the label, has a single nucleotide substitution.

In certain embodiments, additional sequences including DNA, locked nucleic acid (LNA) or RNA bases can be added, deleted, substituted or modified in the primers and probe to confer advantageous properties. The 5' or 3' regions can be modified, specifically one, two, three, four, five, six, seven, eight, nine, ten, or more DNA, locked nucleic acid (LNA) or RNA bases can be added, deleted, or substituted. In preferred embodiments, a 5' CG dimer is added, preferably in the stem region that comprises an endonuclease binding site, to increase the stability of the double-stranded region.

Kits

In certain embodiments, the present compositions and methods of use can further be provided in a kit. The kit can include one or more of the following: one or more primers (FP and/or LP,), one or more probes (AP and/or BP), other reagents (e.g., any described herein, such as enzymes, buffer, nucleotides, or enhancing agents), particularly reagents that one skilled in the art would recognize as necessary or beneficial for LAMP, and instructions for use (e.g., such as those including any method described herein). Each component of the kit can be packaged separately or together. In one instance, the components are packaged together to allow for a single chamber or single test tube reaction.

Enzymes

In certain embodiments, one or more enzymes can be used, including a plurality of polymerases and endonucleases. If the target nucleic acid includes a RNA sequence, or a portion of an RNA sequence, then a reverse transcriptase can be employed to reverse transcribe the RNA target into a DNA (e.g., cDNA) sequence.

Any DNA polymerase with 3'-5' displacement activity that can work at about 50° C. to about 70° C. degree can be used in the subject invention. Exemplary polymerase enzymes include Bst DNA polymerase (including Bst 3.0; New England BioLabs, Inc., Ipswich, Mass.), Bca (exo-) DNA polymerase, DNA polymerase I Klenow fragment, Vent DNA polymerase, Vent (exo-) DNA polymerase (Vent DNA polymerase deficient in exonuclease activity), Vent™ DNA polymerase, 9° N™ polymerase, Deep Vent DNA polymerase, Deep Vent(exo-)DNA polymerase (Deep Vent DNA polymerase deficient in exonuclease activity), 129 phage DNA polymerase, MS-2 phage DNA polymerase, Z-Taq DNA polymerase (Takara Shuzo Co., Ltd.), Taq polymerase, and KOD DNA polymerase (Toyobo Co., Ltd.), as well as variants thereof.

Exemplary endonuclease enzymes include Nb.B srDI, Nt.BspQI, Nt.CviPII, Nt.BstNBI, Nb.Btsl, Nt.AlwI, Nb.BbvCI, Nt.BbvCI, Nb.Bsml, Nb.BssSI, and Nt.BsmAI. Other endonucleases are envisioned for use in the subject invention, particularly nicking endonucleases that function at a temperature of about 50° C. to about 70° C., and the cleavage product of the endonuclease cleavage includes a region of nucleotides at the 5' end of the recognized sequence that can release from amplicons.

Reverse transcriptases useful in the present invention can be any polymerase that exhibits reverse transcriptase activity. Several reverse transcriptases are known in the art and are commercially available (e.g., from Boehringer Mannheim Corp., Indianapolis, Ind.; Life Technologies, Inc., Rockville, Md.; New England Biolabs, Inc., Beverley, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif.). In some embodiments, the reverse transcriptase can be Avian Myeloblastosis Virus reverse transcriptase (AMV-RT), Moloney Murine Leukemia Virus reverse transcriptase (M-MLV-RT), Human Immunovirus reverse transcriptase (HIV-RT), EIAV-RT, RAV2-RT, C. hydrogenoformans DNA Polymerase, rTth DNA polymerase, SUPERSCRIPT I, SUPERSCRIPT II, and mutants, variants and derivatives thereof. It is to be understood that a variety of reverse transcriptases can be used in the present invention, including reverse transcriptases not specifically disclosed above, without departing from the scope or preferred embodiments disclosed herein.

Nucleotide Bases

Nucleotide bases useful in the present invention can be any nucleotide useful in the polymerization of a nucleic acid. Nucleotides can be naturally occurring, unusual, modified, derivative, or artificial. Nucleotides can be unlabeled, or detectably labeled by methods known in the art (e.g., using radioisotopes, vitamins, fluorescent or chemiluminescent moieties, dioxigenin). Preferably the nucleotides are deoxynucleoside triphosphates, dNTPs (e.g., dATP, dCTP, dGTP, dTTP, dITP, dUTP, α-thio-dNITs, biotin-dUTP, fluorescein-dUTP, digoxigenin-dUTP, 7-deaza-dGTP). dNTPs are also well known in the art and are commercially available from venders (e.g., from Boehringer Mannheim Corp., Indianapolis, Ind.; New England Biolabs, Inc., Beverley, Mass.; Pharmacia LKB Biotechnology, Inc., Piscataway, N.J.).

The nucleotides of the present invention can be present in any concentration. In some embodiments, the nucleotides are present in an amount from about 0.001 μM to about 40 about 0.005 μM to about 20 or, preferably, about 0.01 μM to about 4 µM. One of skill in the art will appreciate that other concentrations of nucleotides are useful in the present invention.

Buffering Agents and Salts

Buffering agents and salts useful in the present invention provide appropriate stable pH and ionic conditions for nucleic acid synthesis, e.g., for reverse transcriptase and DNA polymerase activity. A wide variety of buffers and salt solutions and modified buffers are known in the art that can be useful in the present invention, including agents not specifically disclosed herein. Preferred buffering agents include, but are not limited to, Tris-HCl, NaCl, MgCl$_2$, and BSA. Preferred salt solutions include, but are not limited to solutions of, potassium acetate, potassium sulfate, potassium chloride, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, and lithium acetate.

The buffering agents of the present invention can be present in any concentration. In some embodiments, the buffering agent is present in an amount from about 0.01 mM to about 4000 mM, about 0.05 mM to about 2000 mM, or, preferably, about 0.1 mM to about 400 mM. One of skill in the art will appreciate that other concentrations of buffer are useful in the present invention.

Methods of Use

In certain embodiments, the present probes, primers, assays, and methods can be used to detecting any target of interest. In particular, the probes, primers, assays, and methods allow for a single-step reaction. The present compositions and methods can further provide reduced background amplification and/or detection compared to existing methods of nucleotide detection. In some embodiments, the compositions and methods can be configured for sensing a nucleic acid (e.g., DNA or RNA), as well as for detecting a pathogen (e.g., a bacterial pathogen, such as any herein), metabolite, genetic modification, and/or pesticide for any use (e.g., livestock monitoring, crop maintenance, as well as any other agricultural use).

The present compositions and methods can be used to detect any useful targets (e.g., a target nucleic acid or a nucleic acid sequence derived from the target or identifiable as the target). Exemplary targets include a bacterium, such as such as *Bacillus* (e.g., *B. anthracis*), Enterobacteriaceae (e.g., *Salmonella, Escherichia coli, Yersinia pestis, Klebsiella*, and *Shigella*), *Yersinia* (e.g., *Y. pestis* or *Y. enterocolitica*), *Staphylococcus* (e.g., *S. aureus*), *Streptococcus, Gonorrheae, Enterococcus* (e.g., *E. faecalis*), *Listeria* (e.g., *L. monocytogenes*), *Brucella* (e.g., *B. abortus, B. melitensis*, or *B. suis*), *Vibrio* (e.g., *V. cholerae*), *Corynebacterium diphtheria, Pseudomonas* (e.g., *P. pseudomallei* or *P. aeruginosa*), *Burkholderia* (e.g., *B. mallei* or *B. pseudomallei*), *Shigella* (e.g., *S. dysenteriae*), *Rickettsia* (e.g., *R. rickettsii, R. prow azekii*, or *R. typhi*), *Francisella tularensis, Chlamydia psittaci, Coxiella burnetii, Mycoplasma* (e.g., *M. mycoides*), etc.; an allergen, such as mycotoxins, mold spores, or bacterial spores such as *Clostridium botulinum* and *C. perfringens*; a toxin, such as ricin, mycotoxin, tetrodotoxin, anthrax toxin, botulinum toxin, *staphylococcal* entertoxin B, or saxitoxin; a virus, such as *Adenoviridae* (e.g., adenovirus), *Arenaviridae* (e.g., Machupo virus), *Bunyaviridae* (e.g., Hantavirus or Rift Valley fever virus), *Coronaviridae* (e.g., SARS-CoV, MERS-CoV, SARS-CoV-2), *Orthomyxoviridae* (e.g., influenza viruses), *Filoviridae* (e.g., Ebola virus and Marburg virus), *Flaviviridae* (e.g., Japanese encephalitis virus and Yellow fever virus), *Hepadnaviridae* (e.g., hepatitis B virus), *Herpesviridae* (e.g., herpes simplex viruses), *Papovaviridae* (e.g., papilloma viruses), *Paramyxoviridae* (e.g., respiratory syncytial virus, measles virus, mumps virus, or parainfluenza virus), *Parvoviridae, Picornaviridae* (e.g., polioviruses), *Poxviridae* (e.g., variola viruses), *Reoviridae* (e.g., rotaviruses), *Retroviridae* (e.g., human T cell lymphotropic viruses (HTLV) and human immunodeficiency viruses (HIV)), *Rhabdoviridae* (e.g., rabies virus), and *Togaviridae* (e.g., encephalitis viruses, yellow fever virus, and rubella virus)); a protozoon, such as *Cryptosporidium parvum, Encephalitozoa, Plasmodium, Toxoplasma gondii, Acanthamoeba, Entamoeba histolytica, Giardia lamblia, Trichomonas vaginalis, Leishmania*, or *Trypanosoma* (e.g., *T. brucei* and *T. Cruzi*); a helminth, such as cestodes (tapeworms), trematodes (flukes), or nematodes (roundworms, e.g., *Ascaris lumbricoides, Trichuris trichiura, Necator americanus*, or *Ancylostoma duodenale*); a parasite (e.g., any protozoa or helminths described herein); a fungus, such as *Aspergilli, Candidae, Coccidioides immitis*, and *Cryptococci*; a pathogen; an environmental contaminant; a water additive; an agricultural marker; a nucleic acid (e.g., oligonucleotides, polynucleotides, nucleotides, nucleosides, molecules of DNA, or molecules of RNA, including a chromosome, a plasmid, a viral genome, a primer, or a gene of any useful pathogen, such as those described herein); or a genetic modification (e.g., antibiotic resistance marker gene). Targets also include food-borne pathogens, such as *Salmonella* (e.g., *Salmonella Typhimurium*), pathogenic *E. coli* (e.g., O157:H7), *Bacillus* (e.g., *B. cereus*), *Clostridium botulinum, Listeria monocytogenes, Yersinia* (e.g., *Y. enterocolitica*), *Norovirus* (e.g., Norwalk virus), *Shigella, Staphylococcus aureus, Toxoplasma gondii, Vibrio* (e.g., *V. vulnificus, V. cholera, V. parahaemolyticus*), *Campylobacter jejuni*, and *Clostridium perfringens*; and weaponized pathogens, such as *Bacillus anthracis, Yersinia pestis, Francisella tularensis, Brucella* (e.g., *B. suis*), *Burkholderia mallei, Burkholderia pseudomallei, Shigella, Clostridium botulinum, Variola* (e.g., *V. major*), *Filoviridae* (e.g., Ebola virus and Marburg virus), *Arenaviridae* (e.g., Lassa virus and Machupo virus), *Clostridium perfringens*, any food-borne pathogen (e.g., *Salmonella* species, *Escherichia coli* O157:H7, or *Shigella*), *Chlamydia psittaci, Coxiella burnetii, Staphylococcal aureus, Rickettsia* (e.g., *R. prowazekii* or *R. rickettsii*), *Alphavirus* (e.g., Venezuelan equine encephalitis virus, eastern equine encephalitis virus, or western equine encephalitis virus), *Vibrio cholerae, Cryptosporidium parvum, Henipavirus* (e.g., Nipah virus), *Bunyaviridae* (e.g., Hantavirus or Rift Valley fever virus), *Flaviviridae* (e.g., Japanese encephalitis virus and Yellow fever virus), and *Coccidioides* spp.

The test sample can include any useful sample, such as a microorganism, a virus, a bacterium, a fungus, a parasite, a helminth, a protozoon, a cell, tissue, a fluid, a swab, a biological sample (e.g., blood, serum, plasma, saliva, etc.), a plant, an environmental sample (e.g., air, soil, and/or water), etc.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLES

In the examples below, the scheme using a fluorescent, an electroactive loop probe, and a lateral flow loop probe were employed to detect an important drug-resistant gene in many pathogenic bacteria, including, for example, *Salmonella* spp. (such as *Salmonella enterica* subsp. *enterica* serovar Typhimurium (ATCC® 53648™)). leading to antimicrobial resistance. By using a real-time PCR machine to monitored dynamic amplification process with fluorescent Loop probes in reaction, and the product was viewed using agarose gel to separate the products formed, and by using a screen printed carbon electrode to conduct the end-point analysis with electroactive loop probe.

Example 1—Real-Time Detection of Target DNA Using Fluorescent Loop Probe

Figure 1B:
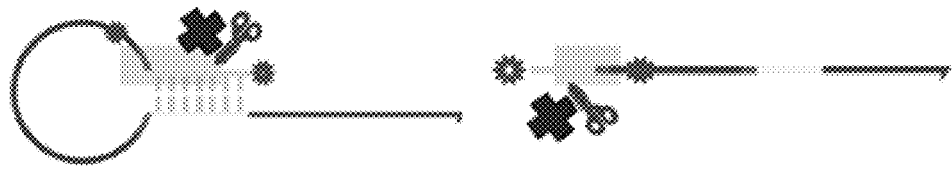
FIG. 1B. Detection principle scheme. In the absence of target nucleic acid, either linear- or loop-shaped probes cannot be cleaved to release the label.
Figure 1C:
FIG. 1C. Detection principle scheme. The loop probe hybridizes to the corresponding target nucleic acid site when present, and a fluorescent readout is released by nicking endonuclease cleavage.

In this example, the real-time detection of the target DNA using a fluorescent loop probe is shown. The detection principle is depicted in FIGS. 1A-1C. FIG. 1A shows the structure of a fluorescent loop probe containing a fluorophore at the 5'end and the corresponding quencher modified on a loop of up to 13 bases to ensure that the probe is quenched. The forward primer is about 18-20 bp, complementary to the template DNA, and the melting point is 61-63° C. The stem region contains the recognition sequence of nicking enzyme Nb.BsrDI. The introduction of a mismatch on the last base pair of the stem before the loop (G base) inhibits the probe cleavage in the absence of the target DNA. A 5' CG dimer was added to the end of the stem to increase the stability of the double stranded region. FIG. 1B shows that both the loop probe and the open circuit state are not susceptible to nicking enzyme in the absence of target. FIG. 1C depicts the target of interest, which, with the help of DNA polymerase, can promote the formation of the double stranded structure. Thus, Nb.BsrDI can make a nick 3 base pairs away from the 5' end of DNA. Because this fragment is too short, it is easily released, and a fluorescence signal is generated.

As shown in FIG. 2A, the template DNA is selected to have two pairs of primer binding sites—one pair of external forward and reverse primers (FP and BP, respectively), and one pair of internal primers consisting of the loop probe (LP) and the auxiliary probe (AP). FP and LP bind to the same strand of dsDNA template, while BP and AP bind to the opposite strand. Notably, thermodynamic calculations can be used to rationally design the inner primers LP and AP, and make them more likely to bind to complementary region first than outer primers FP and BP. The detection process starts from the pre-amplification step, in which the continuous hybridization and re-hybridization of the dsDNA template at 60-65° C. allow one of the internal primers (i.e. LP or AP) to anneal its complementary region on the DNA template, and DNA synthesis is initiated by polymerase. When LP binds to the DNA template, the synthesized complementary strand is shorter than the template DNA, thus exposing the FP binding site upstream of the newly synthesized strand. When the DNA polymerase without exonuclease activity extends FP, the previously bound fragment containing LP is displaced, and the final structure is a double loop stranded DNA (dsDNA), which can participate in a new primer binding and extension cycle.

FIG. 2B describes the process of double loop amplification. The previously formed double-loop product, such as LP', can be extended from the 3' end of the double loop structure to form a hairpin structure with an extended stem region, and in this example, another loop AP would be linearized. In addition, the excess LP probe can also bind to the LP'loop or be extended by the polymerase to form a double stranded product, which can be replaced by the shifted single stranded region extended in the previous step. The single chain region has an AP structure, which then transform into a loop structure, which continues in a similar manner as described above, using redundant AP probes instead of LP probes. The final amplification structure will be the long dsDNA structure of LP'—target AP target tandem repeats. Finally, each loop probe region (LP' and AP) is nicked by Nb.BsrDI and the fluorophore is released. When starting from LP-AP' containing the loop probe, the same structure will be obtained, but tandem repeats of LP target AP'—target will be instead.

Conceptually, the method presented here can be used to detect RNA targets. The amplification process is similar with the one abovementioned, with slight modifications. Prior to amplification, RNA-directed DNA polymerase (i.e. reverse transcriptase) should be added into the reaction and incubated at specific conditions, usually at about 37° C. to about 42° C. for 10-20 min. The cDNA generated from the target RNA can be used as template of amplification and detection. Thus, our method is also suitable for RNA detection with an additional reverse transcription step.

Figure 3A:
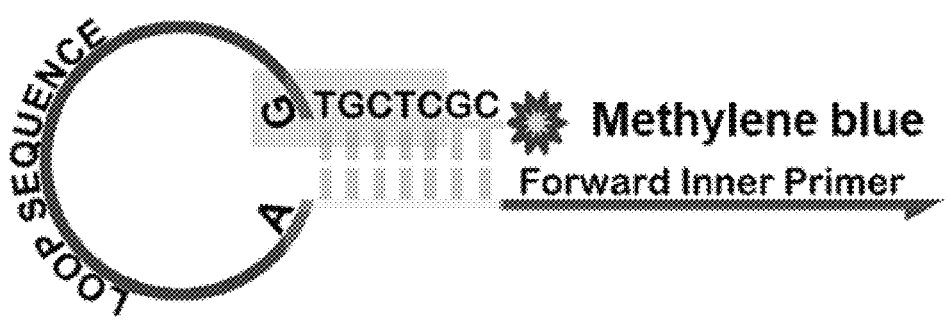
FIG. 3A Detection principle using an electroactive loop probe. The structure of the electroactive-labelled loop probe containing an electroactive-label at the 5' end. The stem region contains the nicking enzyme recognition sequence. The mismatch is introduced into the last G base so that it is not cleaved in the absence of the target nucleic acid. 5'CG dimer was added to the end of the stem to increase the stability of the double stranded region.
Figure 3B:
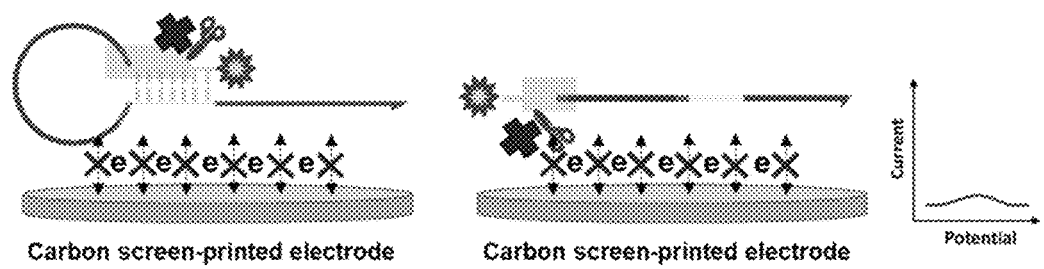
FIG. 3B Detection principle using an electroactive loop probe. In the absence of target nucleic acid, either linear or loop shaped probes cannot be cleaved, and because the loop probe cannot easily diffuse to the electrode surface.
Figure 3C:
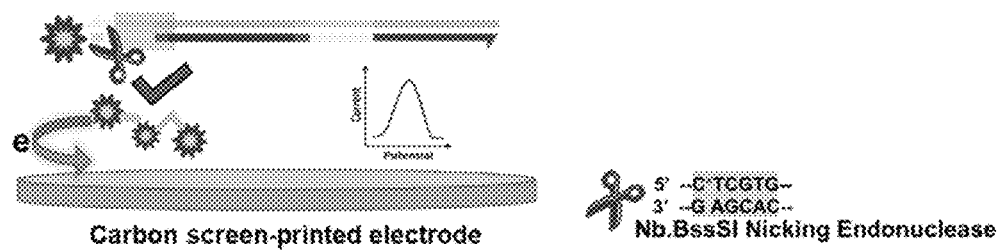
FIG. 3C Detection principle using an electroactive loop probe. When bound to the target nucleic acid, the loop probe is cleaved by the nicking enzyme and an electrochemical readout is ob served.
Figure 4A:
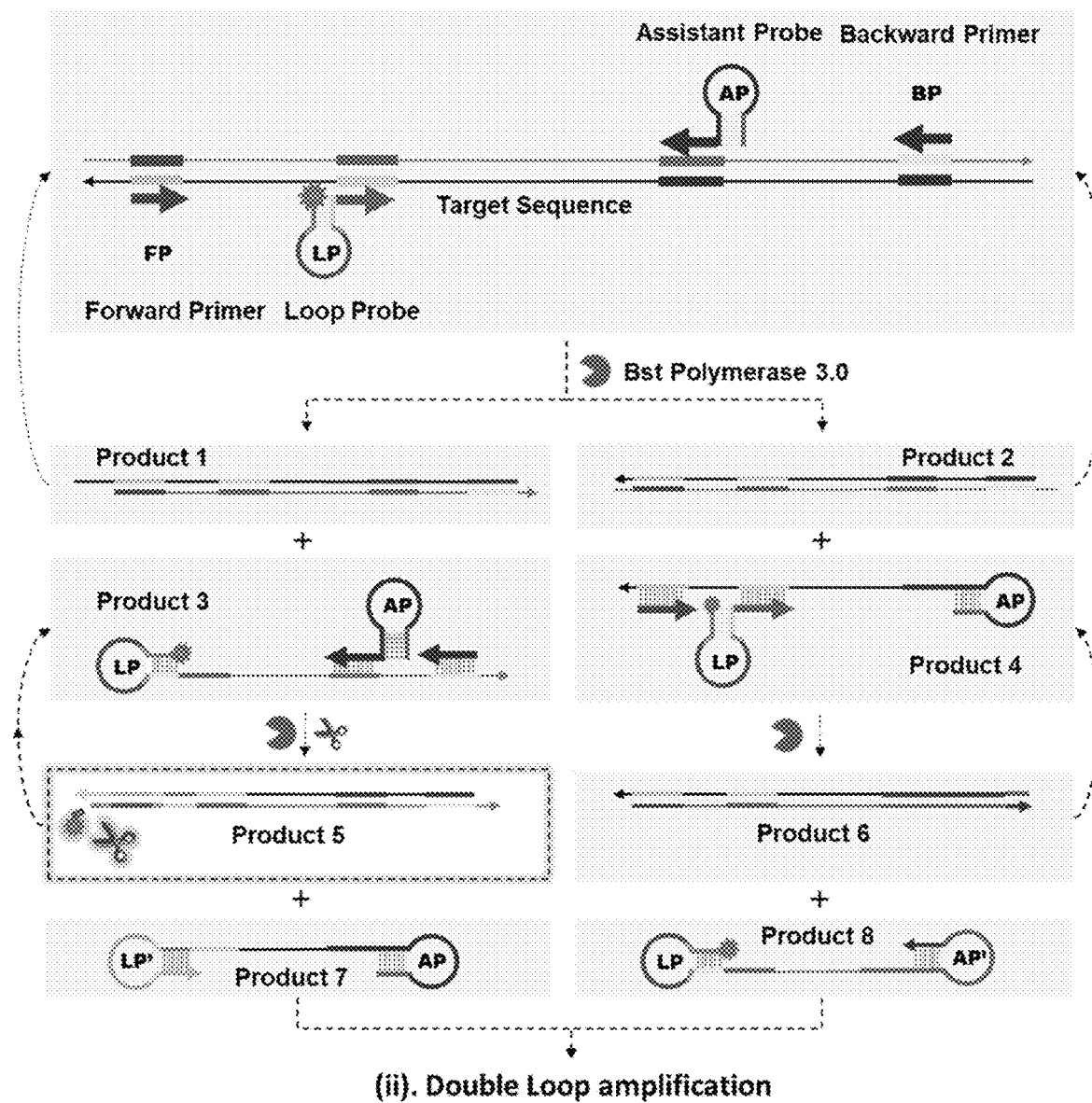
FIG. 4A Detection scheme using an electroactive loop probe. Pre-amplification process. The DNA template is selected to have two pairs of primer binding site—an outer pair of forward and backward primers (FP and BP), and an inner pair of primers consisting of a loop probe (LP) and an assistant probe (AP). The inner primers, LP and AP, are rationally designed such that they are thermodynamically favored to bind to its complementary region first compared to its outer primer counterpart FP and BP, respectively.
Figure 4B:
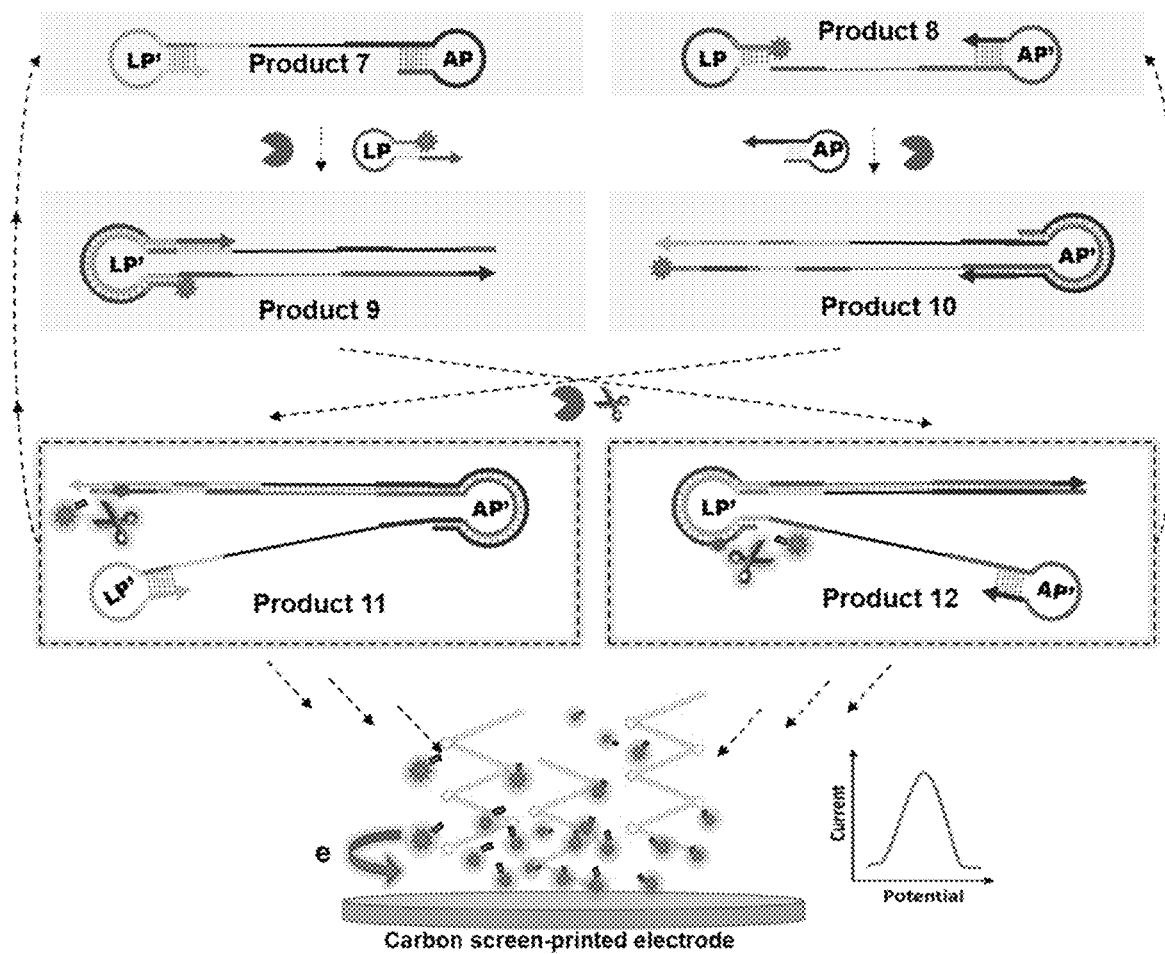
FIG. 4B. Detection scheme using an electroactive loop probe, showing the process and signal readout principle of double loop amplification.

Example 2—Real-Time Detection of Target DNA Using Loop Probe on Carbon Screen Printed Electrodes In this example, a probe labeled with an electroactive molecule is used for real-time detection of target DNA. As shown in FIGS. 3A-3C, the principle of loop probe cleavage is similar to the fluorescence principle in Example 1, with the difference being that it uses the Nb.BssSI nicking enzyme and its specific recognition site in the hydrolysis loop probe modified with an electroactive reporter on the 5' end. This reporter can be methylene blue, ferrocene, among others. Notably, the use of a different nicking enzyme was just for demonstrating its feasibility. The stem and primer sequences are similar to the fluorescently labelled probes described earlier. FIG. 3B shows in an immobilization-free electrochemical biosensor using the method here proposed. Because of steric hindrance, the reporter in the loop probe cannot diffuse to the carbon screen-printed electrode surface. In the presence of a target (FIG. 3C), Nb.BssSI can bind to the recognition site and make a nick, allowing the release of a three-nucleotide fragment carrying an electroactive reporter. This fragment can then diffuse to the electrode and an electrochemical signal is registered using a potentiometer. As shown in FIGS. 4A-4B, the amplification and cleavage process are similar to the previous example, except that the electroactive loop probe is used in lieu of the fluorescent-labelled probe.

Example 3—Colorimetic Paper-Based Detection of Taget DNA Using Lateral Flow Loop Probe In this example, a probe with 5' end modification and inner modification are used for colorimetric paper-based detection. As shown in FIG. 5A, the principle of loop probe cleavage is similar to the fluorescence detection principle in Example 1, with the difference being that it uses the Nb.BssSI nicking enzyme and its specific recognition site in the hydrolysis loop probe. Notably, the use of a different nicking enzyme was just for demonstrating its feasibility. FIG. 5A illustrates the structure of the lateral flow loop probe with 5' end modification and inner modification. These modifications could be 6-FAM, Biotin, Digoxin, among others. The stem and primer sequences are similar to the fluorescently labelled probes described earlier. The lateral-flow readout can be adapted to either signal-on mode or signal-off mode. FIG. 5B shows the scheme of a signal-on design of lateral-flow readout, where the appearance of test band indicates a positive result.

Example 4—Real-Time Detection of Sulfonamide Resistance Gene (Sul 1) Using Fluorescent Loop Probe A. Sequencing
The sequence of primers and probes were listed in following table:

| Oligo name | Sequence (5'-3') |
|---|---|
| Forward primer (SEQ ID NO: 1) | ACCGCGGCGATCGAAAT |
| Backward primer (SEQ ID NO: 2) | GCGCATAGCGCTGGGTT |
| Forward inner primer (loop probe) with HEX label at 5' end and quencher modified thymine at base pair 11 (SEQ ID NO: 3) | HEX-CGCTCGTGAC/iBHQ1dT/ AGCCTGCTCACTCGAACGAGCGCTATTGGTCTCGGTGTC |
| Backward inner primer (assistant probe) (SEQ ID NO: 5) | CGGTCGTGCCACTGCCCTCTATCGACACGACCGCCGAGAAG GTGATTGC |

B. Sensitivity Test.

Figure 6:
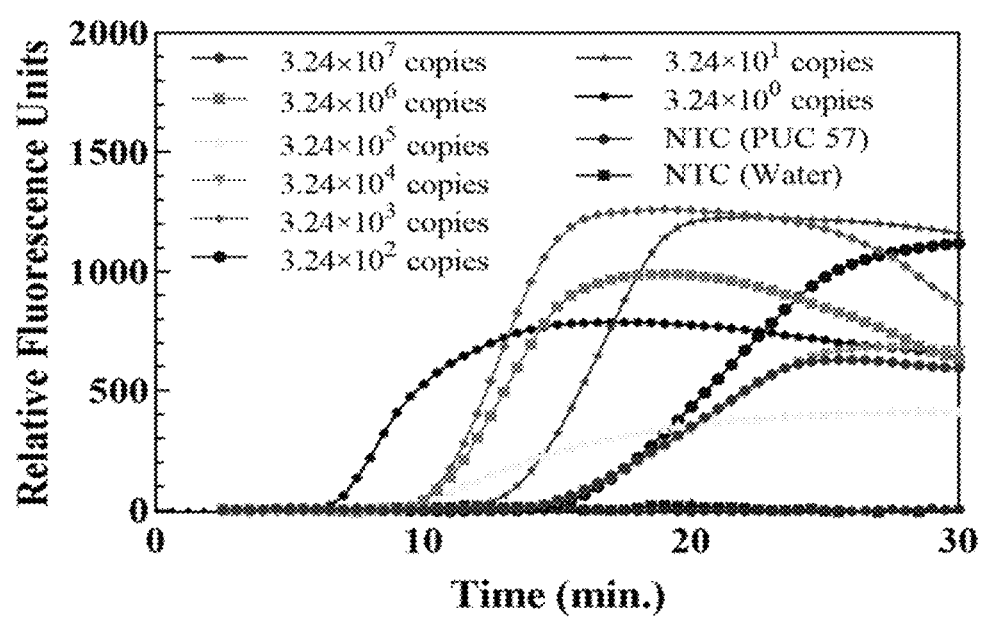
FIG. 6 shows fluorescent signals derived from a cleaved fluorescent label. The signal was found to be detectable after 6 to 15 minutes depending on the concentration of the nucleic acid template in the mixture.

Reactions were carried out in a 25 μl reaction mixture system as followed: 8U Bst 3.0 polymerase, 1U Nb. BssSI nicking endonuclease, 2.5 μl 10×NEB 3.1 buffer, 6 mM MgSO₄, 1.4 mM each dNTP and appropriate nucleic acid template. For one reaction, 1.6 μM fluorescent Loop probe, 1.6 μM assistant probe, 0.2 μM forward primer and 0.2 μM backward primer were used. Lastly, nuclease-free water was added to obtain a final volume of 25 μl. The reactions were performed at 61° C. on Bio-rad™ real-time PCR system. Results show that as the time of amplification increases, fluorescent signals followed a sigmoidal growth curve. The signal was found to be detectable after 6 to 15 minutes depending on the concentration of the nucleic acid template in the mixture. The limit of detection reached up to 3.24 copies/reaction (FIG. 6).

B. Specificity Test.

Reactions were carried out in a 25 μl reaction mixture system as followed: 8U Bst 3.0 polymerase, 1U Nb. BssSI nicking endonuclease, 2.5 μl 10×NEB 3.1 buffer, 6 mM MgSO₄, 1.4 mM each dNTP and appropriate PUC plasmid without target sequence. For one reaction, 1.6 μM fluorescent Loop probe, 1.6 μM assistant probe, 0.2 μM forward primer and 0.2 μM backward primer were used. Lastly, nuclease-free water was added to obtain a final volume of 25 μl. The reactions were performed at 61° C. on Bio-rad™ real-time PCR system. Results show no signal curve even after incubation for 1 hour.

Example 5—Detection of Sulfonamide Resistance Gene (Sul 1) Using Electroactive Loop Probe on Carbon Screen Printed Electrodes A. Sequencing The sequence of primers and probes were listed in following table:

| Oligo name | Sequence (5'-3') |
|---|---|
| Forward primer (SEQ ID NO: 1) | ACCGCGGCGATCGAAAT |
| Backward primer (SEQ ID NO: 2) | GCGCATAGCGCTGGGTT |
| Forward inner primer (loop probe) with methylene blue label at 5' end (SEQ ID NO: 4) | Methylene blue-CGCTCGTGACT AGCCTGCTCACTCGAACGAGCGCTATTGGTCTCGGTGTC |
| Backward inner primer (assistant probe) (SEQ ID NO: 5) | CGGTCGTGCCACTGCCCTCTATCGACACGACCGCCGAGAAG GTGATTGC |

B. Sensitivity Test.

Figure 7:
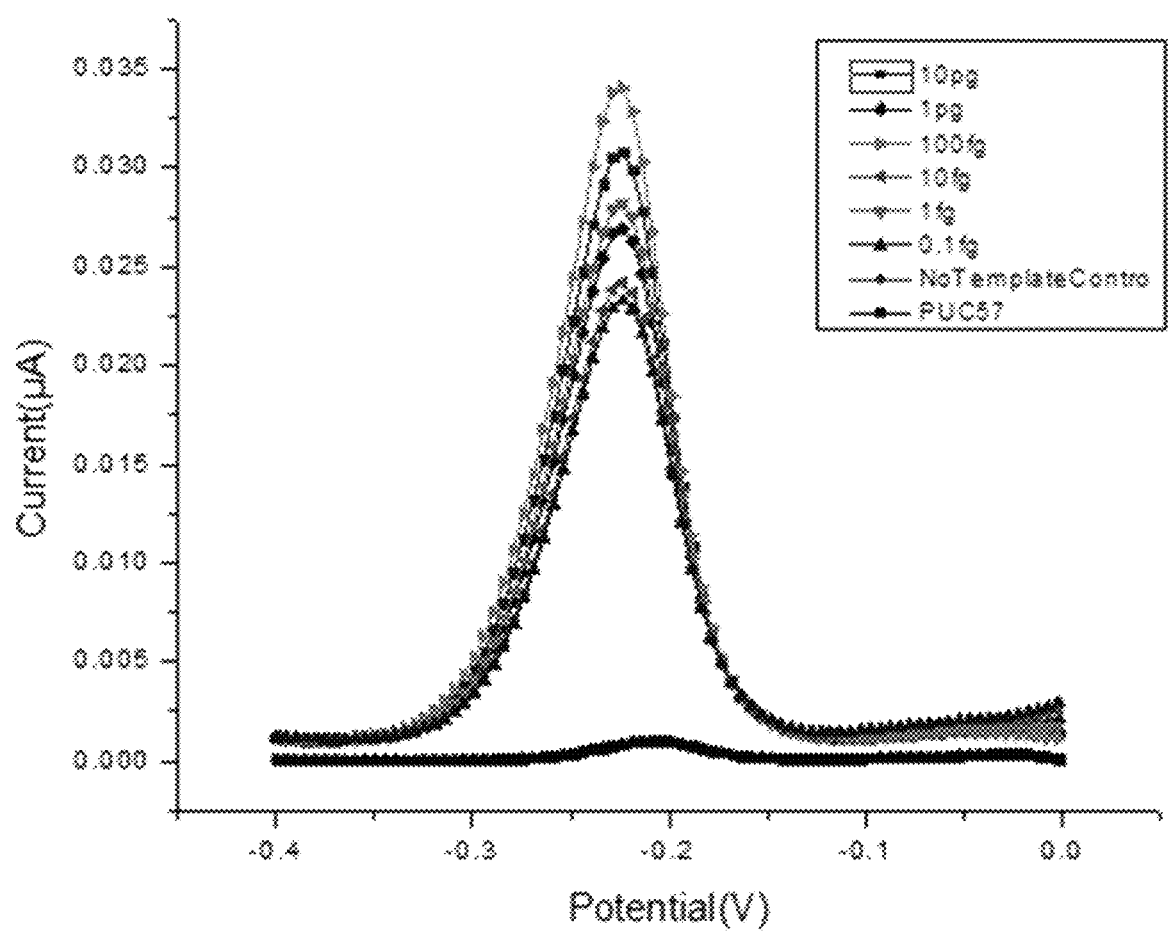
FIG. 7 shows electrolabel signals derived from a cleaved electroactive label. Results show that after 30 mins, the signal of various concentrations of template presented a range of peak height from 0.0240.035 μA.

Reactions were carried out using similar conditions as in the previous example, except that 1.6 μM electroactive loop probe in lieu of the fluorescent-labelled probe. Electrochemical detection was conducted on a 4-array carbon screen printed electrode; and differential pulse voltammetry (DPV) was carried out using a pulse amplitude of 100 mV/s and a scan rate of 25 mV/s. Results show that after 30 mins, the signal of various concentrations of template presented a range of peak height from 0.024~0.035 μA (FIG. 7); and the detection of limit was similar to the previous method (FIG. 6).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

[1] T. Notomi, "Loop-mediated isothermal amplification of DNA," *Nucleic Acids Res.*, vol. 28, no. 12, pp. 63e-63, June 2000.

[2] Y. Mori and T. Notomi, "Loop-mediated isothermal amplification (LAMP): A rapid, accurate, and cost-effective diagnostic method for infectious diseases," *J. Infect. Chemother.*, vol. 15, no. 2, pp. 62-69, 2009.

[3] CURTIS, K. A. et al., "Sequence-Specific Detection Method for Reverse Transcription, Loop-Mediated Isothermal Amplification of HIV-1", Journal of Medical Virology, 2009, 81:966-972, Wiley-Liss, Inc.

[4] Y. P. Wong, S. Othman, Y. L. Lau, S. Radu, and H. Y. Chee, "Loop-mediated isothermal amplification (LAMP): a versatile technique for detection of micro-organisms," *J. Appl. Microbiol.*, vol. 124, no. 3, pp. 626-643, 2018.

[5] Y. Mori, K. Nagamine, N. Tomita, and T. Notomi, "Detection of loop-mediated isothermal amplification reaction by turbidity derived from magnesium pyrophosphate formation.," *Biochem. Biophys. Res. Commun.*, vol. 289, no. 1, pp. 150-154, November 2001.

[6] M. Parida et al., "Rapid detection and differentiation of dengue virus serotypes by a real-time reverse transcription-loop-mediated isothermal amplification assay.," *J. Clin. Microbiol.*, vol. 43, no. 6, pp. 2895-2903, June 2005.

[7] M. Goto, E. Honda, A. Ogura, A. Nomoto, and K. I. Hanaki, "Colorimetric detection of loop-mediated isothermal amplification reaction by using hydroxy naphthol blue," *Biotechniques*, vol. 46, no. 3, pp. 167-172, 2009.

[8] P. Francois et al., "Robustness of a loop-mediated isothermal amplification reaction for diagnostic applications.," *FEMS Immunol. Med. Microbiol.*, vol. 62, no. 1, pp. 41-48, June 2011.

[9] F. Zerilli, C. Bonanno, E. Shehi, G. Amicarelli, D. Adlerstein, and G. M. Makrigiorgos, "Methylation-specific loop-mediated isothermal amplification for detecting hypermethylated DNA in simplex and multiplex formats.," *Clin. Chem.*, vol. 56, no. 8, pp. 1287-1296, August 2010.

[10] Y. Kouguchi, T. Fujiwara, M. Teramoto, and M. Kuramoto, "Homogenous, real-time duplex loop-mediated isothermal amplification using a single fluorophore-labeled primer and an intercalator dye: Its application to the simultaneous detection of Shiga toxin genes 1 and 2 in Shiga toxigenic *Escherichia coli* isolates," *Mol. Cell. Probes*, vol. 24, no. 4, pp. 190-195, August 2010.

[11] N. A. Tanner, Y. Zhang, and T. C. J. Evans, "Simultaneous multiple target detection in real-time loop-mediated isothermal amplification.," *Biotechniques*, vol. 53, no. 2, pp. 81-89, August 2012.

[12] W. Liu et al., "Establishment of an accurate and fast detection method using molecular beacons in loop-mediated isothermal amplification assay.," *Sci. Rep.*, vol. 7, p. 40125, January 2017.

We claim:

1. A method of detecting a target nucleic acid sequence in a sample in real-time, the method comprising:
   a) optionally, reverse transcribing the target nucleic acid sequence in the sample;
   b) combining the sample with a polymerase, an outer pair of primers comprising a forward primer and a backward primer, and an inner pair of primers comprising a loop probe and an assistant probe, to provide a reaction mixture wherein:
      i) the loop probe comprises a first nucleic acid sequence complementary to a first site in the target nucleic acid operably linked to a label and operably linked to two or more endonuclease binding sites, wherein one of the two or more endonuclease binding sites has at least one substituted base pair that inhibits endonuclease digestion of the loop probe, and the assistant probe comprises a second nucleic acid sequence complementary to a second site of the target nucleic acid wherein at least one of the two or more endonuclease binding sites is a nicking endonuclease binding site; and
      ii) the forward primer and the backward primer are complementary to at least a portion of said target nucleic acid;
   c) adding an endonuclease to the reaction mixture; and
   d) amplifying the target nucleic acid sequence, if present, in the reaction mixture, wherein said label is cleaved from the loop probe when a strand of DNA complementary to the loop probe is synthesized and hybridizes to a nucleotide sequence comprising the sequence of the loop probe.

2. The method of claim 1, wherein the label of the loop probe is a fluorescent label and the loop probe further comprises a quencher label operably linked to the first nucleic acid sequence.

3. The method of claim 1, wherein the label of the loop probe is an electrochemically active molecule or lateral flow label molecule.

4. The method of claim 1, wherein the nicking endonuclease binding site is recognized by Nb.BssSI or Nb.BsrDI.

5. The method of claim 1, wherein the loop probe is single-stranded loop DNA with a 3' overhang and a stem region.

6. The method of claim 5, wherein the melting temperature of the 3' overhang is about 50° C. to about 65° C.

7. The method of claim 5, where the melting temperature of the stem region is about 50° C. to about 65° C.

8. The method of claim 5, wherein the stem region comprises a CG dimer.

9. The method of claim 1, wherein the melting temperature of each of the two or more endonuclease binding sites of the loop probe are about 50° C. to about 65° C.

10. The method of claim 1, wherein the polymerase has 5' to 3' displacement activity.

11. The method of claim 1, wherein the polymerase does not have 5' to 3' exonuclease activity.

12. The method of claim 1, wherein the target nucleic acid sequence is double-stranded DNA.

13. The method of claim 1, wherein the target nucleic acid sequence is single-stranded DNA.

14. The method of claim 1, wherein the target nucleic acid sequence is RNA.

15. The method of claim 1, wherein the loop probe and/or the assistant probe is an inner primer, a loop primer, or a loop primer configured for a loop-mediated isothermal amplification reaction.

16. The method of claim 1, wherein the combining step and the amplifying step are conducted in a single reaction chamber and at a constant temperature.

17. The method of claim 1, wherein a signal provided by the cleaved label is determined in real-time.

18. The method of claim 1, wherein the reaction mixture further comprises a buffer, a divalent cation, a deoxynucleotide, a nucleotide, a DNA polymerase, an enhancing agent, and optionally, one or more reagents selected from the group consisting of an endonuclease and a reverse transcriptase.

* * * * *

SEQUENCE LISTING

```
<160> NUMBER OF SEQ ID NOS: 5

<210> SEQ ID NO 1
<211> LENGTH: 17
<212> TYPE: DNA
<213> ORGANISM: Salmonella enterica

<400> SEQUENCE: 1
accgcggcga tcgaaat                                                    17

<210> SEQ ID NO 2
<211> LENGTH: 17
<212> TYPE: DNA
<213> ORGANISM: Salmonella enterica

<400> SEQUENCE: 2
gcgcatagcg ctgggtt                                                    17

<210> SEQ ID NO 3
<211> LENGTH: 50
<212> TYPE: DNA
<213> ORGANISM: Artificial Sequence
<220> FEATURE:
<223> OTHER INFORMATION: nucleotide probes for detecting the Sul1 gene
<220> FEATURE:
<221> NAME/KEY: misc_feature
<222> LOCATION: (1)..(1)
<223> OTHER INFORMATION: HEX label at 5' end
<220> FEATURE:
<221> NAME/KEY: misc_feature
<222> LOCATION: (11)..(11)
<223> OTHER INFORMATION: quencher modified thymine at base pair 11

<400> SEQUENCE: 3
cgctcgtgac tagcctgctc actcgaacga gcgctattgg tctcggtgtc                50

<210> SEQ ID NO 4
<211> LENGTH: 50
<212> TYPE: DNA
<213> ORGANISM: Artificial Sequence
<220> FEATURE:
<223> OTHER INFORMATION: nucleotide probes for detecting the Sul1 gene
<220> FEATURE:
<221> NAME/KEY: misc_feature
<222> LOCATION: (1)..(1)
```

-continued

```
<223> OTHER INFORMATION: Methylene blue label at 5' end

<400> SEQUENCE: 4
cgctcgtgac tagcctgctc actcgaacga gcgctattgg tctcggtgtc          50

<210> SEQ ID NO 5
<211> LENGTH: 49
<212> TYPE: DNA
<213> ORGANISM: Salmonella enterica

<400> SEQUENCE: 5
cggtcgtgcc actgccctct atcgacacga ccgccgagaa ggtgattgc           49
```